United States Patent
Han et al.

(10) Patent No.: US 8,067,562 B2
(45) Date of Patent: Nov. 29, 2011

(54) ISOLATED NUCLEIC ACID MOLECULE COMPRISING THE AMINO ACID SEQUENCE OF SEQ ID NO:1

(75) Inventors: HQ Han, Thousand Oaks, CA (US); Keith Soo-Nyung Kwak, Thousand Oaks, CA (US); Xiaolan Zhou, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 215 days.

(21) Appl. No.: 11/590,962

(22) Filed: Oct. 31, 2006

(65) Prior Publication Data

US 2007/0117130 A1    May 24, 2007

Related U.S. Application Data

(60) Provisional application No. 60/732,270, filed on Nov. 1, 2005.

(51) Int. Cl.
| | |
|---|---|
| *C07H 21/04* | (2006.01) |
| *C12P 21/06* | (2006.01) |
| *C12N 15/00* | (2006.01) |
| *C12N 5/02* | (2006.01) |

(52) U.S. Cl. .................. 536/23.5; 435/69.1; 435/320.1; 435/325

(58) Field of Classification Search ........................ None
See application file for complete search history.

(56) References Cited

U.S. PATENT DOCUMENTS

| | | | |
|---|---|---|---|
| 5,885,794 A | 3/1999 | Mathews et al. | |
| 6,162,896 A | 12/2000 | Mathews et al. | |
| 6,812,339 B1 * | 11/2004 | Venter et al. ............... | 536/24.31 |
| 6,891,082 B2 | 5/2005 | Lee et al. | |
| 2004/0223966 A1 | 11/2004 | Wolfman et al. | |
| 2005/0186593 A1 | 8/2005 | Mathews et al. | |
| 2006/0068468 A1 | 3/2006 | Knopf et al. | |

FOREIGN PATENT DOCUMENTS

WO    WO 00/43781    7/2000

OTHER PUBLICATIONS

Wells, Biochemistry 29:8509-8517, 1990.*
Ngo et al., The Protein Folding Problem and Tertiary Structure Prediction, pp. 492-495, 1994.*
Wang et al. Nucl. Acids Res. 27: 4609-4618, 1999.*
Kaufman et al., Blood 94: 3178-3184, 1999.*
Wigley et al. Reprod Fert Dev 6: 585-588, 1994.*
Campbell et al. Theriogenology 47(1): 63-72, 1997.*
Phillips, A., J Pharm Pharmacology 53: 1169-1174, 2001.*
Longfellow et al, Biochemistry, 29: 278-285, 1990.*
Harrison, C.A., et al., "Antagonists of activin signaling: mechanisms and potential biological applications," *Trends in Endocrinology and Metabolism* 16(2):73-78, Mar. 2005.
Lee, S. and McPherron, A.C., "Regulation of myostatin activity and muscle growth," *Proc. Natl. Acad. Sci. USA* 98(16):9306-9311, Jul. 2001.
Lee, S., et al., "Regulation of muscle growth by multiple ligands signaling through activin type II receptors," *Proc. Natl. Acad. Sci. USA* 102(50):18117-18122, Dec. 2005.
Tobin, J.F., and Celeste, A.J., "Myostatin, a negative regulator of muscle mass: implications for muscle degenerative diseases," *Current Opinion in Pharmacology, Elsevier Science Publishers* 5(3):328-332, Jun. 2005.
Database EMBL Accession No. AY421275, Dec. 13, 2003, "*Homo sapiens* ACVR2B gene, Virtual Transcript, partial sequence, genomic survey sequence."
Database Geneseq Accession No. AAW86245, Feb. 16, 1999, "Mouse ActRIIB4 receptor protein."
Database Geneseq Accession No. ADO43580, Jul. 29, 2004, "Amino acid sequence of ActRIIB."
International Search Report, PCT/US2006/043044, mailed Mar. 15, 2007.

* cited by examiner

*Primary Examiner* — Gyan Chandra
(74) *Attorney, Agent, or Firm* — Lawrence B. Bugaisky

(57) ABSTRACT

The present invention provides novel activin IIB5 receptor polypeptides capable of binding and inhibiting the activities of activin A, myostatin, or GDF-11. The present invention also provides polynucleotides, vectors and host cells capable of producing the receptor polypeptides. Compositions and methods for treating muscle-wasting, metabolic and other disorders are also provided.

11 Claims, 5 Drawing Sheets

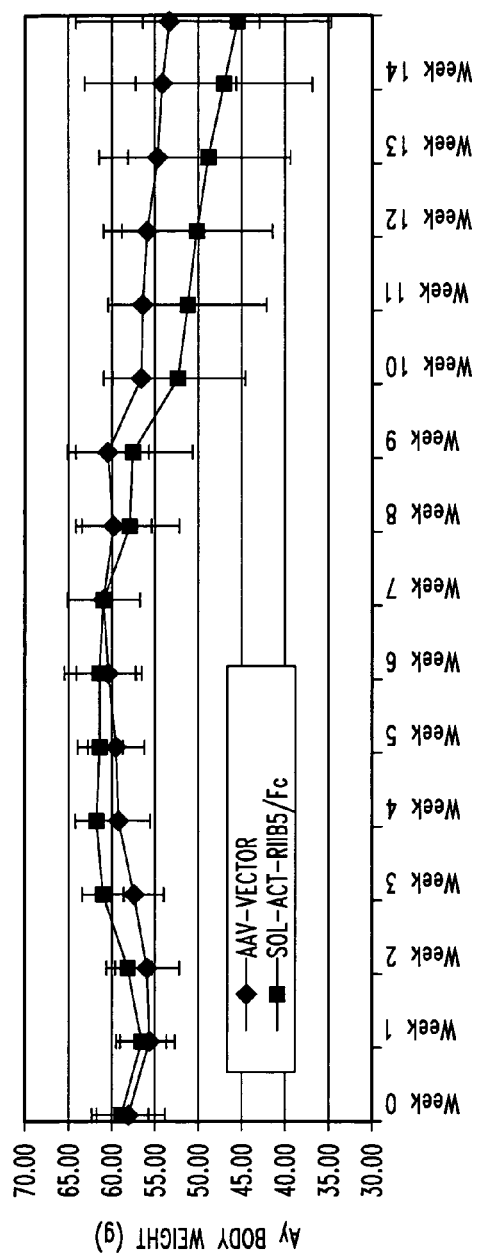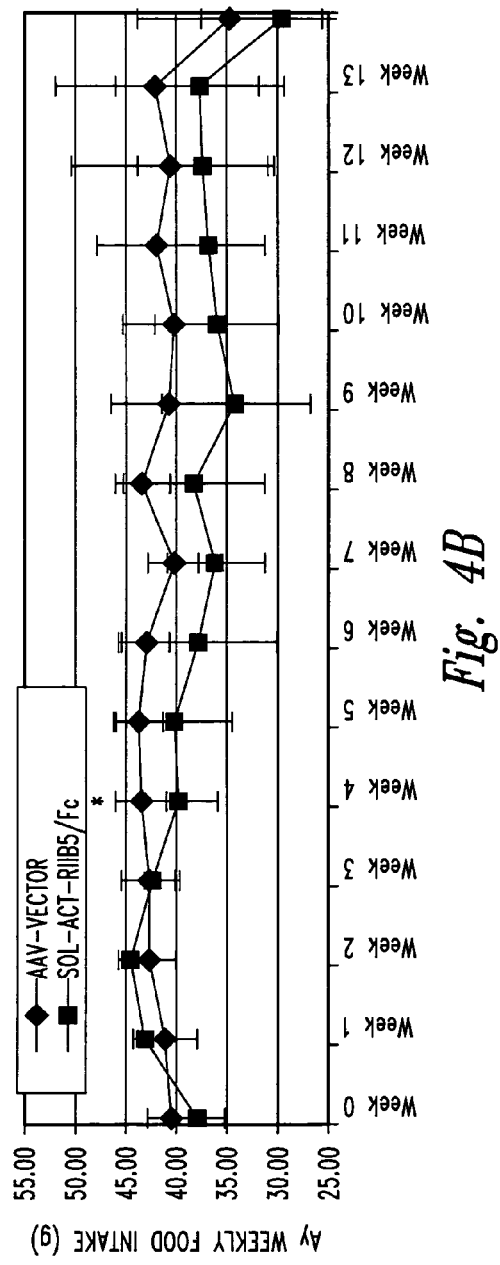

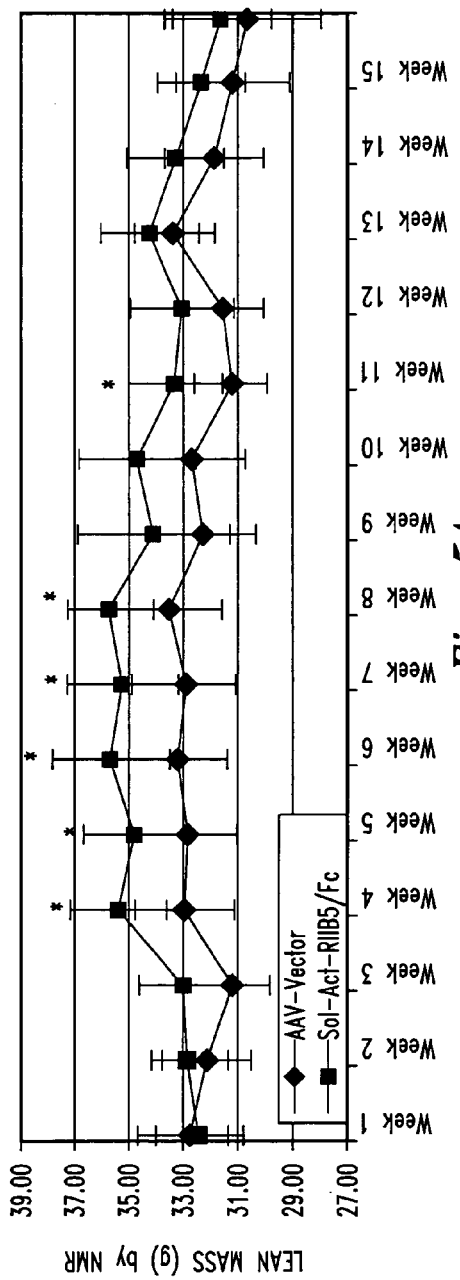
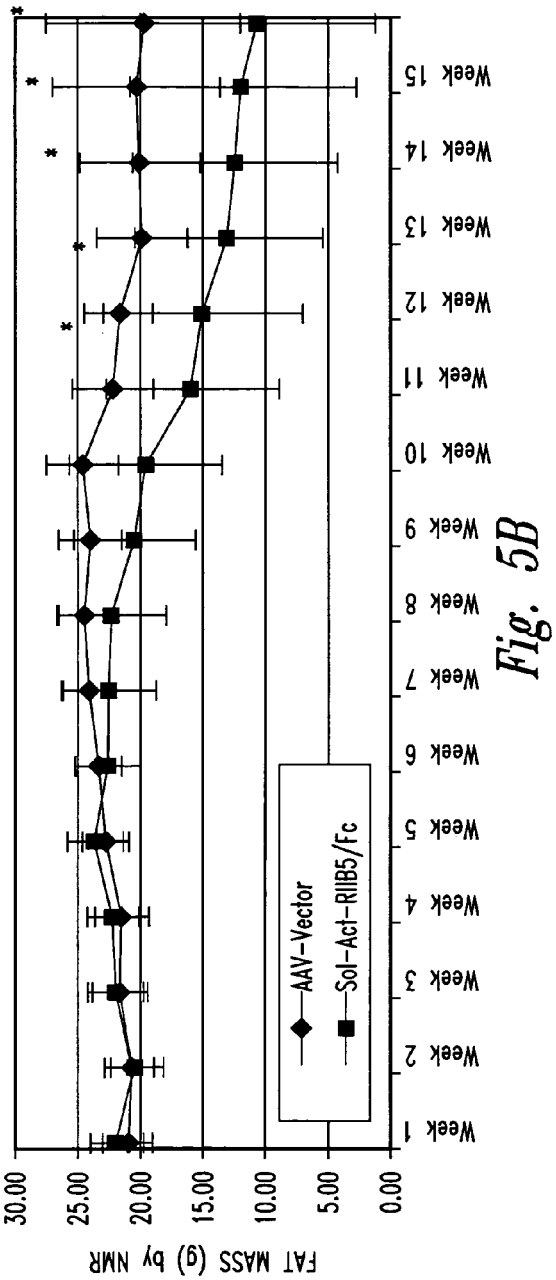
Fig. 5A
Fig. 5B

ISOLATED NUCLEIC ACID MOLECULE COMPRISING THE AMINO ACID SEQUENCE OF SEQ ID NO:1

CROSS-REFERENCE TO RELATED APPLICATIONS

This application claims the benefit of U.S. provisional application Ser. No. 60/732,270, filed Nov. 1, 2005, the entire disclosure of which is relied upon and incorporated by reference.

TECHNICAL FIELD OF THE INVENTION

The technical field of this invention relates to transforming growth factor-β (TGF-β) family members and TGF-β receptors, as well as methods of modulating the activities of TGF-β family members for the treatment of various disorders.

BACKGROUND OF THE INVENTION

The transforming growth factor β (TGF-β) family of proteins includes the transforming growth factors-β (TGF-β), activins, bone morphogenic proteins (BMP), nerve growth factors (NGFs), brain-derived neurotrophic factor (BDNF), and growth/differentiation factors (GDFs). These family members are involved in the regulation of a wide range of biological processes including cell proliferation, differentiation, and other functions. Activins were originally discovered as gonadal peptides involved in the regulation of follicle stimulating hormone synthesis, and are now believed to be involved in the regulation of a number of biological activities including control of section and expression of anterior pituitary hormones such as FSH, GH, and ACTH, neuron survival, hypothalamic oxytocin secretion, erythropoiesis, placental and gonadal steroidogenesis, early embryonic development, and proliferation of some types of tumors. Activins A, B and AB are the homodimers and heterdimer respectively of two polypeptide chains, βA and βB (Vale et al. Nature 321, 776-779 (1986), Ling et al., Nature 321, 779-782 (1986)). These two β chains can also dimerize with a related α chain giving rise to inhibins A and B respectively (Mason et al, Nature 318, 659-663 (1986)). It is well established that inhibins are necessary for maintaining normal function in many tissues, particularly those associated with reproductive functions. In these tissues inhibins oppose many, but not all, of the activin activities.

Growth/differentiation factor 8 (GDF-8), also referred to as myostatin, is a TGF-β family member expressed for the most part in the cells of developing and adult skeletal muscle tissue. Myostatin appears to play an essential role in negatively controlling skeletal muscle growth (McPherron et al. Nature (London) 387, 83-90 (1997)). Antagonizing myostatin has been shown to increase lean muscle mass in animals (McFerron et al, supra, Zimmers et al, Science 296:1486 (2002)).

Another member of the TGF-β family of proteins is a related growth/differentiation factor, GDF-11. GDF-11 has approximately 90% identity of the amino acid sequence of myostatin. GDF-11 has a role in the axial patterning in developing animals (Oh et al, Genes Dev 11: 1812-26 (1997)), and also appears to play a role in skeletal muscle development and growth. However, the postnatal role of GDF-11 is not currently understood.

A family of transmembrane serine/threonine kinases are known to act as receptors for activins and other TGF-β family members. These receptors fall into two distinct subfamilies known as type I and type II receptors that act cooperatively to bind ligand and transduce signal (Attisano et al., Mol Cell Biol 16 (3), 1066-1073 (1996)). Most TGF-β ligands are believed bind first to a type II receptor and this ligand/type II receptor complex then recruits a type I receptor (Mathews, L S, Endocr Rev 15:310-325 (1994); Massague, Nature Rev: Mol Cell Biol. 1, 169-178 (2000)). The type II receptor kinase then phosphorylates and activates the type I receptor kinase, which in turn phosphorylates the Smad proteins. Activins initially bind their type II receptors ActRIIA for activin A, or ActRIIB for activin B. This is followed by the recruitment, phosphorylation and subsequent activation of the type I receptor, activin-like kinase 4 (ALK4). On activation, ALK4 binds and then phosphorylates a subset of cytoplasmic Smad proteins (Smad2 and Smad3) that produce signal transduction for activins (Derynck, R et al. Cell 95, 737-740 (1998)).

Cross-linking studies have determined that myostatin is capable of binding the activin type II receptors ActRIIA and ActRIIB in vitro (Lee et al. PNAS USA 98:9306-11 (2001)). There is also evidence that GDF-11 binds to both ActRIIA and ActRIIB (Oh et al., Genes Dev 16:2749-54 (2002)).

TGF-β proteins are known to be associated with a variety of disease states and antagonizing these proteins may be useful as therapeutic treatments for the disease states. In particular antagonizing several TGF-β proteins simultaneously may be particularly effective for treating certain diseases. The present invention provides a novel composition of matter and methods of using the composition of matter as a treatment for muscle-related and other disorders.

SUMMARY OF THE INVENTION

The present invention provides a protein comprising human activin receptor IIB5 (designated ActRIIB5) polypeptides. In one embodiment, the protein comprises polypeptides having an amino acid sequence set forth in SEQ ID NO: 2. In another embodiment the protein comprises a polypeptide having an amino acid sequence with at least about 80% or greater identity to SEQ ID NO: 2, wherein the polypeptide is capable of binding myostatin, activin A, or GDF-11. In another embodiment, the protein comprises a polypeptide having an amino acid sequence with at least about 80% or greater identity to SEQ ID NO: 2, wherein the C terminal of the polypeptide consists of the amino acid sequence set forth in SEQ ID NO: 3, and wherein the polypeptide is capable of binding myostatin, activin A, or GDF-11. In another embodiment, the protein comprises a polypeptide having an amino acid sequence with at least about 80% or greater identity to SEQ ID NO: 2, wherein the C terminal of the polypeptide has an amino acid sequence with at about least 80% or greater identity to SEQ ID NO: 3, and wherein the polypeptide is capable of binding myostatin, activin A, or GDF-11. In one embodiment, the polypeptide lacks an ActRIIB5 signal sequence. In another embodiment, the protein comprises a polypeptide encoded by the polynucleotide having the sequence set forth in SEQ ID NO: 1.

In another embodiment, the protein of the present invention comprises ActRIIB5 polypeptides fused to one or more heterologous polypeptides. In one embodiment, the fused ActRIIB5 polypeptides lack a signal sequence. In one embodiment the ActRIIB5 polypeptides are fused to the heterologous polypeptides via one or more linker sequences. In another embodiment the heterologous polypeptides comprise an Fc domain. In another embodiment, the Fc domain is connected to the ActRIIB5 polypeptides by at least one linker sequence. In another embodiment, ActRIIB5 polypeptides are attached to a non-protein carrier molecule such as a PEG molecule.

In another aspect the present invention provides an isolated nucleic acid molecule comprising a polynucleotide encoding an ActRIIB5 polypeptide. In one embodiment, the nucleic acid molecule comprises (a) a polynucleotide having the nucleic acid sequence set forth in SEQ ID NO: 1 or its complement. In another embodiment, the nucleic acid molecule comprises (b) a polynucleotide encoding a polypeptide consisting of the amino acid sequence set forth in SEQ ID NO: 2 or its complement. In another embodiment, the nucleic acid molecule comprises (c) a polynucleotide which hybridizes to (a) or (b) under conditions of at least moderate stringency in about 50% formamide, 6×SSC at about 42° C. and washing conditions of about 60° C., 0.5×SSC, 0.1% SDS, and wherein the encoded polypeptide comprises a C terminal having an amino acid sequence set forth in SEQ ID NO: 3, and wherein the polypeptide is capable of binding myostatin, activin A, or GDF-11. In another embodiment, the nucleic acid molecule comprises the polynucleotide of (c) wherein the C terminal of the encoded polypeptide has an amino sequence at least about 80% or greater identity to SEQ ID NO: 3, and wherein the polypeptide is capable of binding myostatin, activin A, or GDF-11. In another embodiment, the nucleic acid molecule comprises a polynucleotide having at least about 80% or greater identity to SEQ ID NO: 1.

In another embodiment, the nucleic acid molecule of the present invention further comprises polynucleotides encoding at least one heterologous protein in frame with the polynucleotides encoding an ActRIIB5 polypeptide. In one embodiment, nucleic acid molecule comprises polynucleotides encoding linker peptide sequences attaching the ActRIIB5 polypeptide to at least one heterologous protein. In another embodiment the heterologous protein is an Fc polypeptide. The present invention further provides a vector comprising the nucleic acid molecules set forth above, as well as a host cell genetically engineered to express the nucleic acid molecules described above, and methods for producing the ActIIRB5 protein.

The present invention further provides a composition containing the protein of the present invention. In one embodiment, the composition is a pharmaceutical composition containing the protein in admixture with a pharmaceutically acceptable carrier.

In another aspect, the present invention provides a method of inhibiting the TGF-β proteins myostatin, activin or GDF-11 activity in vitro and in vivo by contacting the proteins with an ActRIIB5 polypeptide. In another aspect the present invention provides a method of increasing lean muscle mass and strength, and a method of increasing the ratio of lean muscle to fat in a subject in need thereof by administering an effective amount of the composition containing ActRIIB5 proteins to the subject. In one embodiment of this method, the subject is a food animal.

In another aspect, the present invention provides a method of treating or preventing a muscle wasting disease in a subject suffering from such a disorder by administering a therapeutic composition containing an ActRIIB5 protein to the subject. The muscle wasting disease includes or results from, but is not limited to, the following conditions: muscular dystrophy, amyotrophic lateral sclerosis, congestive obstructive pulmonary disease, chronic heart failure, cancer cachexia, chemical cachexia, HIV/AIDS, renal failure, uremia, rheumatoid arthritis, age-related sarcopenia, organ atrophy, carpal tunnel syndrome, androgen deprivation, and muscle-wasting due to inactivity such as prolonged bed rest, spinal chord injury, stroke, bone fracture, aging. The muscle wasting may also result from events such as weightlessness from space flight, insulin resistance, muscle wasting due to burns, androgen deprivation, and other disorders. In another aspect, the present invention provides a method of treating a disease correlated to expression of activin A. In one embodiment, the disease is cancer. In another aspect, the present invention provides a method of treating a metabolic disorder comprising administering a therapeutic composition to a subject in need of such treatment, wherein the metabolic disorder is selected from diabetes, obesity, impaired glucose tolerance, hyperglycemia, androgen deprivation, metabolic syndrome, and bone loss. In another aspect, the present invention provides a method of gene therapy comprising administering a vector encoding the ActRIIB5 proteins of the present invention protein to a subject in need thereof, wherein the vector is capable of expressing the ActRBII5 polypeptide in the subject.

The present invention further provides a method of detecting and quantitating the TGF-β proteins myostatin, GDF-11 or activin A by contacting these proteins with an ActRIIB5 polypeptide and detecting the polypeptide.

BRIEF DESCRIPTION OF THE FIGURES

FIG. 4A shows a decrease in body weight over time for Ay obese mice injected with AAV-ActRIIB5/Fc compared with a control group of Ay obese mice injected with AAV-empty vectors over a period of about three months. FIG. 4B shows a decrease in weekly food intake for the same group of AAV-ActRIIB5 mice compared with the control group over the same period of time.

FIG. 5A shows the change in lean body mass over time for Ay obese mice injected with AAV-ActRIIB5/Fc compared with a control group of Ay obese mice injected with AAV-empty vector over a period of about three months. FIG. 5B shows a large decrease in fat mass for the AAV-ActRIIB5/Fc mice compared with a control group of AAV-empty mice over the same period of time.

DETAILED DESCRIPTION OF THE INVENTION

Figure 1:
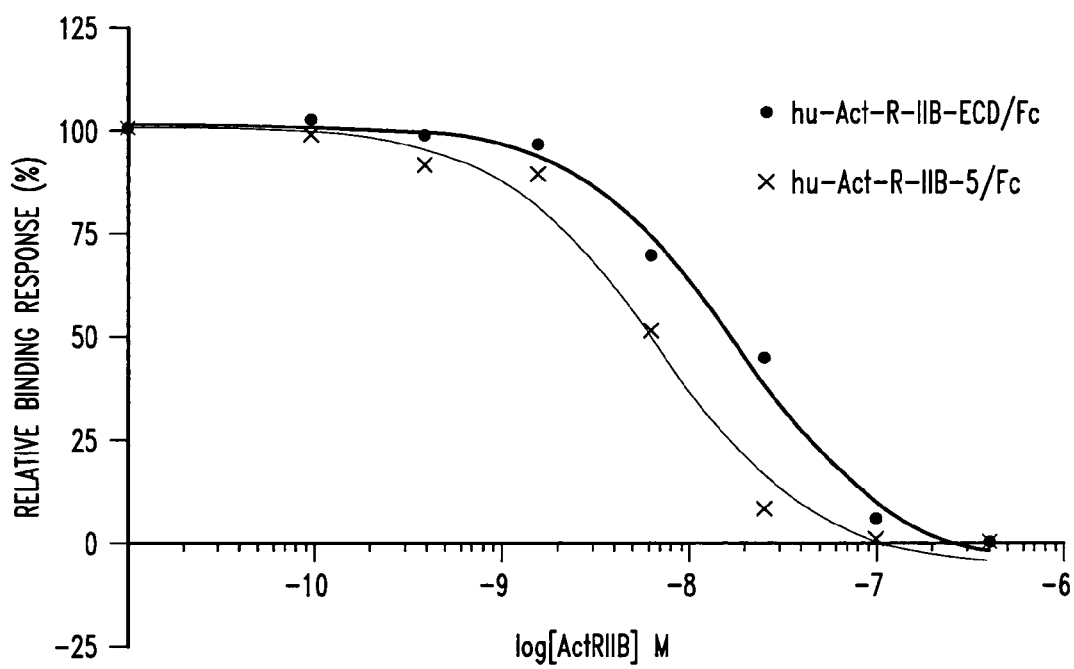
FIG. 1 shows the results of Biacore® assay determination of $EC_{50}$ for ActRIIB5/Fc compared to ActRIIB ECD/Fc.

The present invention provides a novel human activin receptor designated activin receptor IIB5 (ActRIIB5). This receptor is characterized by its ability to bind to three TGF-β proteins, myostatin (GDF-8), activin A, and GDF-11, and to inhibit the activities of these proteins.

As used herein the term "TGF-β family members" or "TGF-β proteins" refers to the structurally related growth factors of the transforming growth factor family including activins, and growth and differential factor (GDF) proteins (Kinglsey et al. Genes Dev. 8: 133-146 (1994), McPherron et al. Growth factors and cytokines in health and disease, Vol. 1B, D. LeRoith and C. Bondy. ed., JAI Press Inc., Greenwich, Conn., USA: pp 357-393). GDF-8, also referred to as myostatin, is now know to be a negative regulator of skeletal muscle tissue (McPherron et al. PNAS USA 94:12457-12461 (1997)). Myostatin is synthesized as an inactive preproprotein complex approximately 375 amino acids in length, having GenBank Accession No: AAB86694 for human. The precursor protein is activated by proteolytic cleavage at a tetrabasic processing site to produce an N-terminal inactive prodomain and an approximately 109 amino acid C-terminal protein which dimerizes to form a homodimer of about 25 kDa. This homodimer is the mature, biologically active protein (Zimmers et al., Science 296, 1486 (2002)). As used herein, the term "prodomain" or "propeptide" refers to the inactive N-terminal protein which is cleaved off to release the active C-terminal protein. As used herein the term "myostatin" or "mature myostatin" refers to the mature, biologically active C-terminal polypeptide, in monomer, dimer or other form, as well as biologically active fragments or related polypeptides including allelic variants, splice variants, and fusion peptides and polypeptides. The mature myostatin has been reported to have 100% sequence identity among many species including human, mouse, chicken, porcine, turkey, and rat (Lee et al., PNAS 98, 9306 (2001)). As used herein GDF-11 refers to the BMP protein having Swisspro accession number O95390, as well as variants and species homologs of that protein. GDF-11 has approximately 90% identity to myostatin at the amino acid level. GDF-11 is involved in the regulation of anterior/posterior patterning of the axial skeleton (McPherron et al, Natr Genet 22 (93): 260-264 (1999); Gamer et al, Dev. Biol. 208 (1), 222-232 (1999)) but postnatal functions are unknown. Activin A is the homodimer of the polypeptide chains βA. As used herein the term "activin A" refers to the activin protein having GenBank Accession No: NM_002192, as well as variants and species homologs of that protein.

Activin Receptors

As used herein, the term "activin type II B receptor" (ActRIIB) refers to the human precursor activin receptor having accession number NP_001097 for protein or any variants or homologs of this receptor. The human ActRIIB precursor polynucleotide and amino acid sequences are set forth in SEQ ID NO: 4 and 5 respectively. A variation of ActRIIB is set forth in SEQ ID NO: 6, wherein arginine at position 64 has been replaced with alanine. SEQ ID NO: 5 is referred to as the R form and SEQ ID NO: 6 is referred to as the A form. The extracellular domain of ActRIIB (ActRIIB-ECD) is represented by amino acids 1 through 124 of SEQ ID NO: 5 and 6. Additional murine isoforms for this receptor have been identified as muActRIIB1, muActRIIB2, muActRIIB3 and muActRIIB4.

The present invention provides a novel human activin receptor designated activin receptor IIB5 (ActRIIB5). This receptor is characterized by the C terminal sequence set forth in SEQ ID NO: 3. The cDNA of this receptor was isolated as described in Example 1, and was found to be missing the 152 nucleotide bases corresponding to exon 4. This receptor is further characterized as missing the transmembrane region encoded by exon 4 of the ActRIIB. This receptor is further characterized as being a soluble, secreted instead of a membrane bound receptor. The receptor is further characterized as having the ability to bind and inhibit the activity of any one of activin A, myostatin, or GDF-11.

The present invention provides isolated proteins which comprise ActIIB5 receptor polypeptides. As used herein the term "isolated" refers to a nucleic acid molecule purified to some degree from endogenous material. In one embodiment, the protein comprises ActRIIB5 polypeptides having the amino acid sequence set forth in SEQ ID NO: 2, and variants and derivatives of this polypeptide, which retain the activity of the polypeptide of SEQ ID NO: 2. In one embodiment, the protein comprises a polypeptide having at least about 80% identity, at least about 85% identity, at least about 90% identity, at least about 95% identity, at least about 98% identity, or at least about 99% identity to the amino acid sequence set forth in SEQ ID NO: 2, wherein the polypeptide retains the activity of the polypeptide of SEQ ID NO: 2. In another embodiment, the protein comprises the ActRIIB5 polypeptides described above wherein the polypeptide has a C terminal comprising the amino acid sequence set forth in SEQ ID NO: 3, and wherein the polypeptide retains the activity of the polypeptide of SEQ ID NO: 2. In another the embodiment, the protein comprises the ActRIIB5 polypeptides described above wherein the C terminal has an amino acid sequence having at least about 80%, at least about 85%, at least about 90%, at least about 95%, at least about 98%, or at least about 99% identity to SEQ ID NO: 3, wherein the polypeptide retains the activity of the polypeptide of SEQ ID NO: 2. In one embodiment, the ActRIIB5 polypeptide lacks a signal sequence of SEQ ID NO: 2, for example, amino acids 1 to 17 of SEQ ID NO: 2.

As used herein the term "variant" refers a polypeptide having one or more amino acid inserted, deleted or substituted into the original amino acid sequence, but having a sequence which remains substantially similar to SEQ ID NO: 2, and which retain the activities of ActRIIB5 polypeptides SEQ ID NO: 2. As used herein fragments of the polypeptides which retain the activity of the polypeptides are included in the term "variants". For the purposes of the present invention, "substantially similar" is at least about 80% identical to the amino acid sequence, at least about 85% identical, at least about 90% identical, at least about 95% identical, at least about 98% identical, at least about 99% identical to the amino acid sequence set forth in SEQ ID NO: 2, and retain the biological activities of the polypeptide of SEQ ID NO: 2. Amino acid substitutions which are conservative substitutions are unlikely to affect biological activity are considered identical for purposes of this invention and include the following: Ala for Ser, Val for Ile, Asp for Glu, Thr for Ser, Ala for Gly, Ala for Thr, Ser for Asn, Ala for Val, Ser for Gly, Tyr for Phe, Ala for Pro, Lys for Arg, Asp for Asn, Leu for Ile, Leu for Val, Ala for Glu, Asp for Gly, and the reverse. (See, for example, Neurath et al., The Proteins, Academic Press, New York (1979)). Additional information regarding phenotypically silent amino acid exchanges can be found in Bowie et al., 1999, Science 247:1306-1310. Amino acid substitutions also include substitutions in SEQ ID NO: 2 of non-naturally occurring amino acids, D-amino acids, altered amino acids, or peptidomimetics. Amino acid substitutions also includes non-conservative amino acid substitutions, such as neutral hydrophobic for neutral polar, acidic for basic, and other class substitutions, provided that the substituted polypeptides retain the activities of the polypeptides having the amino acid sequence in SEQ ID NO: 2. Variants further include modifications to the C and N termini which arise from processing due to expression in various cell types such as mammalian cells, *E. coli*, yeasts and other recombinant host cells. Variants further include polypeptide fragments and polypeptides comprising inactivated N-glycosylation site(s), inactivated protease processing site(s), or conservative amino acid substitution(s), of the polypeptide sequence set forth in SEQ ID NO: 2.

Identity and similarity of related peptides and polypeptides can be readily calculated by known methods. Such methods include, but are not limited to, those described in Computational Molecular Biology, Lesk, A. M., ed., Oxford University Press, New York (1988); Biocomputing: Informatics and Genome Projects, Smith, D. W., ed., Academic Press, New York (1993); Computer Analysis of Sequence Data, Part 1, Griffin, A. M., and Griffin, H. G., eds. Humana Press, New Jersey (1994); Sequence Analysis in Molecular Biology, von Heinje, G., Academic Press (1987); Sequence Analysis Primer, Gribskov, M. and Devereux, J., eds., M. Stockton Press, New York (1991); and Carillo et al., SIAM J. Applied Math, 48:1073 (1988). Methods of determining the relatedness or percent identity of two polypeptides are designed to give the largest match between the sequences tested. Preferred computer program methods to determine identity between two sequences include, but are not limited to, the GCG program package, including GAP (Devereux et al., Nucl. Acid. Res., 12:387 (1984); Genetics Computer Group, University of Wisconsin, Madison, Wis., BLASTP, BLASTN, and FASTA (Altschul et al., J. Mol. Biol., 215:403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra (1990)). The well-known Smith Waterman algorithm may also be used to determine identity.

As used herein the term "derivative" of the ActRIIB5 polypeptides refers to the attachment of at least one additional chemical moiety, or at least one additional polypeptide to form covalent or aggregate conjugates such as glycosyl groups, lipids, acetyl groups, or C-terminal or N-terminal fusion proteins, conjugation to PEG molecules, and other modifications which are described more fully below.

As used herein, the term an "ActRIIB5 polypeptide activity" or "a biological activity of ActRIIB5 polypeptide" refers to one or more in vitro or in vivo activities of the ActRIIB5 polypeptides including but not limited to those demonstrated in the Examples below. Activities of the ActRIIB5 polypeptides include, but are not limited to, the ability to bind to myostatin or activin A or GDF-11, the ability to reduce or neutralize an activity of myostatin or activin A or GDF-11. For example, pMARE C2C12 cell-based assay described in Example 3 below measures activin A neutralizing activity, myostatin neutralizing activity, and GDF-11 neutralizing activity. In vivo activities include but are not limited to increasing body weight, increasing lean muscle mass, and decreasing fat mass as demonstrated in animal models below. Biological activities further include reducing or preventing cachexia caused by certain types of tumors, and preventing metastasis of certain tumor cells. Further discussion of ActRIIB5 polypeptide activities is provided below.

The proteins of the present invention further comprise heterologous proteins attached to the ActRIIB5 polypeptide either directly or through a linker sequence to form a fusion protein. As used herein the term "fusion protein" refers to a protein having a heterologous polypeptide attached via recombinant DNA techniques. Heterologous proteins include but are not limited to Fc polypeptides, his tags, and leucine zipper domains to promote oligomerization and stabilization of the ActRIIB5 polypeptides as described in, for example, WO 00/29581, which is herein incorporated by reference. As used herein the term "Fc" or "Fc polypeptide" refers to polypeptides containing the Fc domain of an antibody. The "Fc domain" refers to the portion of the antibody that is responsible for binding to antibody receptors on cells. An Fc domain can contain one, two or all of the following: the constant heavy 1 domain ($C_H1$), the constant heavy 2 domain ($C_H2$), the constant heavy 3 domain ($C_H3$), and the hinge region. The Fc domain of the human IgG1, for example, contains the $C_H2$ domain, and the $C_H3$ domain and hinge region, but not the $C_H1$ domain. Truncated forms of such polypeptides containing the hinge region that promotes dimerization are also included. See, for example, C. A. Hasemann and J. Donald Capra, Immunoglobins: Structure and Function, in William E. Paul, ed. One Fc is a fully human Fc which may originate from any of the immunoglobulins, such as IgG1 and IgG2. However, Fc molecules that are partially human, or originate from non-human species are also included herein. Fc molecules may be made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgA2). The term "Fc" as used herein is used to refer to the monomeric, dimeric, and multimeric forms. As used herein, the term "Fc variant" refers to a modified form of a native Fc sequence. Fc variants may be constructed for example, by substituting or deleting residues, inserting residues or truncating portions containing the site. The inserted or substituted residues may also be altered amino acids, such as peptidomimetics or D-amino acids.

The proteins of the present invention can optionally further comprise a "linker" group. Linkers serve primarily as a spacer between a polypeptide and a second heterologous protein or other type of fusion or between two or more ActRIIB5 polypeptides. In one embodiment, the linker is made up of amino acids linked together by peptide bonds, preferably from 1 to 20 amino acids linked by peptide bonds, wherein the amino acids are selected from the 20 naturally occurring amino acids. One or more of these amino acids may be glycosylated, as is understood by those in the art. In one embodiment, the 1 to 20 amino acids are selected from glycine, alanine, proline, asparagine, glutamine, and lysine. Preferably, a linker is made up of a majority of amino acids that are sterically unhindered, such as glycine and alanine. Exemplary linkers are polyglycines (particularly $(Gly)_5$, $(Gly)_8$, poly(Gly-Ala), and polyalanines.

The linkers of the present invention are also non-peptide linkers. For example, alkyl linkers such as —NH—$(CH_2)_s$-C(O)—, wherein s=2-20 can be used. These alkyl linkers may further be substituted by any non-sterically hindering group such as lower alkyl (e.g., $C_1$-$C_6$) lower acyl, halogen (e.g., Cl, Br), CN, $NH_2$, phenyl, etc.

The proteins of the present invention can also be attached to a non-protein molecule for the purpose of conferring desired properties such as reducing degradation and/or increasing half-life, reducing toxicity, reducing immunogenicity, and/or increasing the biological activity of the ActRIIB polypeptides. Exemplary molecules include but are not limited to linear polymers such as polyethylene glycol (PEG), polylysine, a dextran; a lipid; a cholesterol group (such as a steroid); a carbohydrate, or an oligosaccharide molecule.

In another aspect, the present invention provides isolated nucleic acid molecules comprising polynucleotides encoding the ActRIIB5 polypeptides of the present invention. As used herein the term "isolated" refers to nucleic acid molecules purified to some degree from endogenous material. In one embodiment, the nucleotide acid molecule of the present invention comprises a polynucleotide encoding SEQ ID NO: 2. Due to the known degeneracy of the genetic code, wherein more than one codon can encode the same amino acid, a DNA sequence can vary from that shown in SEQ ID NO: 1, and still encode a polypeptide having the amino acid sequence of SEQ ID NO: 2. Such variant DNA sequences can result from silent mutations occurring during production, or can be the product of deliberate mutagenesis of SEQ ID NO: 2. In another embodiment the nucleic acid molecule comprises a polynucleotide encoding a polypeptide having at least about 80% identity to SEQ ID NO: 2, at least about 90% identity to SEQ ID NO: 2, at least about 95% identity to SEQ ID NO: 2, at least about 99% identity to SEQ ID NO: 2.

The percent identity may be determined by visual inspection and mathematical calculation. Alternatively, the percent identity of two nucleic acid sequences can be determined by comparing sequence information using the GAP computer program, version 6.0 described by (Devereux et al., Nucl. Acids Res., 12:387 (1984)) and available from the University of Wisconsin Genetics Computer Group (UWGCG). The preferred default parameters for the GAP program include: (1) a comparison matrix (containing a value of 1 for identities and 0 for non-identities) for nucleotides, and the weighted comparison matrix of (Gribskov and Burgess, Nucl. Acids Res., 14:6745 (1986)), as described by (Schwartz and Dayhoff, eds., Atlas of Protein Sequence and Structure, National Biomedical Research Foundation, pp. 353-358 (1979)); (2) a penalty of 3.0 for each gap and an additional 0.10 penalty for each symbol in each gap; and (3) no penalty for end gaps. Other programs used by one skilled in the art of sequence comparison may also be used.

In another embodiment the nucleic acid molecule of the present invention comprises a polynucleotide having the polynucleotide sequence set forth in SEQ ID NO: 1, or the complementary strand of SEQ ID NO: 1. In another embodiment, the present invention provides nucleic acid molecules which hybridize under stringent or moderate conditions with the polypeptide-encoding regions of SEQ ID NO: 1, wherein the encoded polypeptide comprises a C terminal amino acid sequence as set forth in SEQ ID NO: 3, and wherein the encoded polypeptide maintains an activity of ActRIIB5 polypeptides.

In another embodiment, the present invention provides nucleic acid molecules which hybridize under stringent or moderate conditions with the polypeptide-encoding regions of SEQ ID NO: 1, wherein the encoded polypeptide comprises a C terminal amino acid sequence having at least about 80% identity, at least about 85% identity, at least about 90% identity, at least about 95% identity, at least about 98% identity, at least about 99% identity to the amino acid sequence set forth in SEQ ID NO: 3, and wherein the encoded polypeptide has at least one activity of ActRIIB5 polypeptides.

As used herein, conditions of moderate stringency can be readily determined by those having ordinary skill in the art based on, for example, the length of the DNA. The basic conditions are set forth by (Sambrook et al. Molecular Cloning: A Laboratory Manual, 2ed. Vol. 1, pp. 1.101-104, Cold Spring Harbor Laboratory Press, (1989)), and include use of a prewashing solution for the nitrocellulose filters 5×SSC, 0.5% SDS, 1.0 mM EDTA (pH 8.0), hybridization conditions of about 50% formamide, 6×SSC at about 42° C. (or other similar hybridization solution, such as Stark's solution, in about 50% formamide at about 42° C.), and washing conditions of about 60° C., 0.5×SSC, 0.1% SDS. Conditions of high stringency can also be readily determined by the skilled artisan based on, for example, the length of the DNA. Generally, such conditions defined as "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. Other conditions include hybridizing and washing at approximately 68° C., 0.2×SSC, 0.1% SDS. The skilled artisan will recognize that the temperature and wash solution salt concentration can be adjusted as necessary according to factors such as the length of the sequence. See Sambrook, Fritsch & Maniatis, Molecular Cloning: A Laboratory Manual (2nd ed., Cold Spring Harbor Laboratory, 1989); Anderson et al., Nucleic Acid Hybridisation: A Practical Approach, Ch. 4 (IRL Press Limited).

Nucleic acid molecules of the invention include DNA in both single-stranded and double-stranded form, as well as the RNA complement thereof. DNA includes, for example, cDNA, genomic DNA, synthetic DNA, DNA amplified by PCR, and combinations thereof. Genomic DNA may be isolated by conventional techniques, such as by using the cDNA of SEQ ID NO: 1, or a suitable fragment thereof, as a probe. Genomic DNA encoding ActRIIB5 polypeptides is obtained from genomic libraries which are available for a number of species. Synthetic DNA is available from chemical synthesis of overlapping oligonucleotide fragments followed by assembly of the fragments to reconstitute part or all of the coding regions and flanking sequences. RNA may be obtained from procaryotic expression vectors which direct high-level synthesis of mRNA, such as vectors using T7 promoters and RNA polymerase. cDNA is obtained from libraries prepared from mRNA isolated from various tissues that express ActRIIB5. The DNA molecules of the invention include full length genes as well as polynucleotides and fragments thereof. The full length gene may also include sequences encoding the N-terminal signal sequence.

The invention also provides methods of producing and identifying ActRIIB5 polynucleotides. The well-known polymerase chain reaction (PCR) procedure may be employed to isolate and amplify a DNA sequence encoding a desired protein fragment. Oligonucleotides that define the desired termini of the DNA fragment are employed as 5' and 3' primers. The oligonucleotides may additionally contain recognition sites for restriction endonucleases, to facilitate insertion of the amplified DNA fragment into an expression vector. PCR techniques are described in Saiki et al., Science, 239:487 (1988); Wu et al., Recombinant DNA Methodology, eds., Academic Press, Inc., San Diego, pp. 189-196 (1989); and Innis et al., PCR Protocols: A Guide to Methods and Applications, eds., Academic Press, Inc. (1990).

In another aspect of the present invention, expression vectors containing the nucleic acid sequences are also provided, and host cells transformed with such vectors and methods of producing the ActRIIB5 polypeptides are also provided. The term "expression vector" refers to a plasmid, phage, virus or vector for expressing a polypeptide from a polynucleotide sequence. Vectors for the expression of ActRII5 polypeptides contain at a minimum sequences required for vector propagation and for expression of the cloned insert. An expression vector comprises a transcriptional unit comprising an assembly of (1) a genetic element or elements having a regulatory role in gene expression, for example, promoters or enhancers, (2) a sequence that encodes ActRIIB5 polypeptides to be transcribed into mRNA and translated into protein, and (3) appropriate transcription initiation and termination sequences. These sequences may further include a selection marker. Vectors suitable for expression in host cells are readily available and the nucleic acid molecules are inserted into the vectors using standard recombinant DNA techniques. Such vectors can include promoters which function in specific tissues, and viral vectors for the expression of ActRIIB5 in targeted human or animal cells. Some exemplary expression vectors suitable for expression of ActRIIB5 include, but are not limited to, pDSRα, (described in WO 90/14363, herein incorporated by reference) and its derivatives, containing ActRIIB5 polynucleotides, and pDC323 or pDC324 vectors (described in Bianchi et al, Biotech and Bioengineering, Vol 84(4):439-444 (2003)) containing ActRII5 polynucleotides, as well as additional suitable vectors known in the art or described below, are provided by the present invention.

The application further provides methods of making ActRIIB5 polypeptides and proteins. A variety of other expression/host systems may be utilized. These systems include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Mammalian host cells may be preferred when post-translational modifications such as glycosylation and polypeptide processing are important for activity. Mammalian expression allows for the production of secreted or soluble polypeptides which may be recovered from the growth medium.

Using an appropriate host-vector system, ActRIIB5 proteins and polypeptides are produced recombinantly by culturing a host cell transformed with an expression vector containing the nucleic acid molecules of the present invention under conditions allowing for production. Transformed cells can be used for long-term, high-yield protein production. Once such cells are transformed with vectors that contain selectable markers as well as the desired expression cassette, the cells can be allowed to grow for 1-2 days in an enriched media before they are switched to selective media. The selectable marker is designed to allow growth and recovery of cells that successfully express the introduced sequences. Resistant clumps of stably transformed cells can be proliferated using tissue culture techniques appropriate to the cell line employed. An overview of expression of recombinant proteins is found in Methods of Enzymology, v. 185, Goeddell, D. V., ed., Academic Press (1990).

In some cases, such as in expression using procaryotic systems, the expressed polypeptides of this invention may need to be "refolded" and oxidized into a proper tertiary structure and disulfide linkages generated in order to be biologically active. Refolding can be accomplished using a number of procedures well known in the art. Such methods include, for example, exposing the solubilized polypeptide to a pH usually above 7 in the presence of a chaotropic agent. The selection of chaotrope is similar to the choices used for inclusion body solubilization, however a chaotrope is typically used at a lower concentration. Exemplary chaotropic agents are guanidine and urea. In most cases, the refolding/oxidation solution will also contain a reducing agent plus its oxidized form in a specific ratio to generate a particular redox potential which allows for disulfide shuffling to occur for the formation of cysteine bridges. Some commonly used redox couples include cysteine/cystamine, glutathione/dithiobisGSH, cupric chloride, dithiothreitol DTT/dithiane DTT, and 2-mercaptoethanol (bME)/dithio-bME. In many instances, a co-solvent may be used to increase the efficiency of the refolding. Commonly used cosolvents include glycerol, polyethylene glycol of various molecular weights, and arginine.

The proteins and polypeptides of the present can be synthesized in solution or on a solid support in accordance with conventional techniques. Various automatic synthesizers are commercially available and can be used in accordance with known protocols. See, for example, Stewart and Young (supra); Tam et al., J Am Chem Soc, 105:6442, (1983); Merrifield, Science 232:341-347 (1986); Barany and Merrifield, *The Peptides*, Gross and Meienhofer, eds, Academic Press, New York, 1-284; Barany et al., Int J Pep Protein Res, 30:705

It is necessary to purify the proteins and polypeptides of the present invention. Protein purification techniques are well known to those of skill in the art. These techniques involve, at one level, the crude fractionation of the proteinaceous and non-proteinaceous fractions. Having separated the peptide polypeptides from other proteins, the peptide or polypeptide of interest can be further purified using chromatographic and electrophoretic techniques to achieve partial or complete purification (or purification to homogeneity). Analytical methods particularly suited to the preparation of polypeptides or the present invention are ion-exchange chromatography, exclusion chromatography; polyacrylamide gel electrophoresis; isoelectric focusing. A particularly efficient method of purifying peptides is fast protein liquid chromatography or even HPLC. The term "isolated polypeptide" or "purified polypeptide" as used herein, is intended to refer to a composition, isolatable from other components, wherein the polypeptide is purified to any degree relative to its naturally-obtainable state. A purified polypeptide therefore also refers to a polypeptide that is free from the environment in which it may naturally occur. Generally, "purified" will refer to a polypeptide composition that has been subjected to fractionation to remove various other components, and which composition substantially retains its expressed biological activity. Where the term "substantially purified" is used, this designation will refer to a peptide or polypeptide composition in which the polypeptide or peptide forms the major component of the composition, such as constituting about 50%, about 60%, about 70%, about 80%, about 90%, about 95% or more of the proteins in the composition.

Various methods for quantifying the degree of purification of polypeptide will be known to those of skill in the art in light of the present disclosure. These include, for example, determining the specific binding activity of an active fraction, or assessing the amount of peptide or polypeptide within a fraction by SDS/PAGE analysis. A preferred method for assessing the purity of a polypeptide fraction is to calculate the binding activity of the fraction, to compare it to the binding activity of the initial extract, and to thus calculate the degree of purification, herein assessed by a "-fold purification number." The actual units used to represent the amount of binding activity will, of course, be dependent upon the particular assay technique chosen to follow the purification and whether or not the polypeptide or peptide exhibits a detectable binding activity.

Various techniques suitable for use in purification will be well known to those of skill in the art. These include, for example, precipitation with ammonium sulphate, PEG, antibodies (immunoprecipitation) and the like or by heat denaturation, followed by centrifugation; chromatography steps such as affinity chromatography (e.g., Protein-A-Sepharose), ion exchange, gel filtration, reverse phase, hydroxylapatite and affinity chromatography; isoelectric focusing; gel electrophoresis; and combinations of these techniques. As is generally known in the art, it is believed that the order of conducting the various purification steps may be changed, or that certain steps may be omitted, and still result in a suitable method for the preparation of a substantially purified polypeptide.

Antibodies

The present invention further includes antibodies which specifically bind to the ActRIIB5 receptor polypeptides of the present invention. As used herein the term "specifically binds" refers to antibodies having a binding affinity (Ka) for ActRIIB5 polypeptides of $10^6$ $M^{-1}$ or greater. As used herein, the term "antibody" refers to intact antibodies including polyclonal antibodies (see, for example Antibodies: A Laboratory Manual, Harlow and Lane (eds), Cold Spring Harbor Press, (1988)), and monoclonal antibodies (see, for example, U.S. Pat. Nos. RE 32,011, 4,902,614, 4,543,439, and 4,411,993, and Monoclonal Antibodies: A New Dimension in Biological Analysis, Plenum Press, Kennett, McKearn and Bechtol (eds.) (1980)). As used herein, the term "antibody" also refers to a fragment of an antibody such as F(ab), F(ab'), F(ab')$_2$, Fv, Fc, and single chain antibodies which are produced by recombinant DNA techniques or by enzymatic or chemical cleavage of intact antibodies. The term "antibody" also refers to bispecific or bifunctional antibodies, which are an artificial hybrid antibody having two different heavy/light chain pairs and two different binding sites. Bispecific antibodies can be produced by a variety of methods including fusion of hybridomas or linking of Fab' fragments. (See Songsivilai et al, Clin. Exp. Immunol. 79:315-321 (1990), Kostelny et al., J. Immunol. 148:1547-1553 (1992)). As used herein the term "antibody" also refers to chimeric antibodies, that is, antibodies having a human constant antibody immunoglobin domain coupled to one or more non-human variable antibody immunoglobin domain, or fragments thereof (see, for example, U.S. Pat. No. 5,595,898 and U.S. Pat. No. 5,693,493). Antibodies also refers to "humanized" antibodies (see, for example, U.S. Pat. No. 4,816,567 and WO 94/10332), minibodies (WO 94/09817), maxibodies, and antibodies produced by transgenic animals, in which a transgenic animal containing a proportion of the human antibody producing genes but deficient in the production of endogenous antibodies are capable of producing human antibodies (see, for example, Mendez et al., Nature Genetics 15:146-156 (1997), and U.S. Pat. No. 6,300,129). The term "antibodies" also includes multimeric antibodies, or a higher order complex of proteins such as heterdimeric antibodies, and anti-idiotypic antibodies. "Antibodies" also includes anti-idiotypic antibodies. The antibodies against ActRIIB5 can be used, for example, to identify and quantitate ActRIIB5 in vitro and in vivo.

Pharmaceutical Compositions

Pharmaceutical compositions containing the ActRIIB5 polypeptides and proteins of the present invention are also provided. Such compositions comprise a therapeutically or prophylactically effective amount of the polypeptide in admixture with pharmaceutically acceptable materials, and physiologically acceptable formulation materials. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. (Remington's Pharmaceutical Sciences, 18$^{th}$ Edition, A. R. Gennaro, ed., Mack Publishing Company, 1990).

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the polypeptide. For example, suitable compositions may be water for injection, physiological saline solution for parenteral administration.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefore. In one embodiment of the present invention, compositions may be prepared for storage by mixing the selected composition having the desired degree of purity with optional formulation agents (Remington's Pharmaceutical Sciences, supra) in the form of a lyophilized cake or an aqueous solution. Further, the therapeutic composition may be formulated as a lyophilizate using appropriate excipients such as sucrose.

The formulations can be delivered in a variety of methods, for example, by inhalation therapy, orally, or by injection. When parenteral administration is contemplated, the therapeutic compositions for use in this invention may be in the form of a pyrogen-free, parenterally acceptable aqueous solution comprising the desired polypeptide in a pharmaceutically acceptable vehicle. A particularly suitable vehicle for parenteral injection is sterile distilled water in which a polypeptide is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for injectable administration may be formulated in aqueous solutions, preferably in physiologically compatible buffers such as Hanks' solution, ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions. In another embodiment, a pharmaceutical composition may be formulated for inhalation. Inhalation solutions may also be formulated with a propellant for aerosol delivery. In yet another embodiment, solutions may be nebulized. Pulmonary administration is further described in PCT Application No. PCT/US94/001875, which describes pulmonary delivery of chemically modified proteins.

It is also contemplated that certain formulations may be administered orally. In one embodiment of the present invention, molecules that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the therapeutic molecule. Diluents, flavorings, low melting point waxes, vegetable oils, lubricants, suspending agents, tablet disintegrating agents, and binders may also be employed. Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate. Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Additional pharmaceutical compositions will be evident to those skilled in the art, including formulations involving polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate (Sidman et al., Biopolymers, 22:547-556 (1983), poly(2-hydroxyethyl-methacrylate) (Langer et al., J. Biomed. Mater. Res., 15:167-277, (1981); Langer et al., Chem. Tech., 12:98-105(1982)), ethylene vinyl acetate (Langer et al., supra) or poly-D(−)-3-hydroxybutyric acid (EP 133,988). Sustained-release compositions also include liposomes, which can be prepared by any of several methods known in the art. See e.g., Eppstein et al., PNAS (USA), 82:3688 (1985); EP 36,676; EP 88,046; EP 143,949.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the polypeptide is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. Polypeptide compositions may be preferably injected or administered intravenously. Long-acting pharmaceutical compositions may be administered every 3 to 4 days, every week, or biweekly depending on the half-life and clearance rate of the particular formulation. The frequency of dosing will depend upon the pharmacokinetic parameters of the polypeptide in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

The route of administration of the pharmaceutical composition is in accord with known methods, e.g. orally, through injection by intravenous, intraperitoneal, intracerebral (intraparenchymal), intracerebroventricular, intramuscular, intraocular, intraarterial, intraportal, intralesional routes, intramedullary, intrathecal, intraventricular, transdermal, subcutaneous, or intraperitoneal; as well as intranasal, enteral, topical, sublingual, urethral, vaginal, or rectal means, by sustained release systems or by implantation devices. Where desired, the compositions may be administered by bolus injection or continuously by infusion, or by implantation device. Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In some cases, the ActRIIB5 polypeptides of the present invention can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

ActRIIB5 gene therapy in vivo is also envisioned wherein a nucleic acid molecule encoding ActRIIB5, or a variant or derivative of ActRIIB5 is introduced directly into the subject. For example, a nucleic acid sequence encoding an ActRIIB5 is introduced into target cells via local injection of a nucleic acid construct with or without an appropriate delivery vector, such as an adeno-associated virus vector. Alternative viral vectors include, but are not limited to, retroviruses, adenovirus, herpes simplex, virus and papilloma virus vectors. Physical transfer of the virus vector may be achieved in vivo by local injection of the desired nucleic acid construct or other appropriate delivery vector containing the desired nucleic acid sequence, liposome-mediated transfer, direct injection (naked DNA), or microparticle bombardment (gene-gun).

Uses of ActRIIB5 Compositions

The present invention provides methods and compositions for reducing or neutralizing the amount or activity of myostatin, activin A, or GDF-11 in vivo and in vitro by contacting the proteins with an ActRIIB5 protein. The Examples below demonstrate that the ActRIIB5 proteins have a high affinity for myostatin, activin A, and GDF-11, and are capable of reducing and inhibiting the biological activities of myostatin, activin A and GDF-11. The Examples demonstrate that ActRIIB5 have a higher activity compared with ActRIIB-ECD as demonstrated by the $IC_{50}$ values in Example 3, and the biological response in animals is superior for the ActRIIB5 animals compared with the ActRIIB-ECD animals as demonstrated in Examples 5 and 6.

In one aspect, the present invention provides methods and reagents for treating myostatin-related and/or activin A related disorders in a subject in need thereof by administering an effective dosage of an ActRIIB5 composition to the subject. As used herein the term "subject" refers to any animal, such as mammals including humans.

The compositions of the present invention have been shown to increase lean muscle mass as a percentage of body weight and decreases fat mass as percentage of body weight in animal models as shown in the Examples below.

The disorders that can be treated by an ActRIIB5 composition include but are not limited to various forms of muscle wasting, as well as metabolic disorders such as diabetes and related disorders, and bone degenerative diseases such as osteoporosis. Muscle wasting disorders include dystrophies such as Duchenne's muscular dystrophy, progressive muscular dystrophy, Becker's type muscular dystrophy, Dejerine-Landouzy muscular dystrophy, Erb's muscular dystrophy, and infantile neuroaxonal muscular dystrophy. Additional muscle wasting disorders arise from chronic diseases or disorders such as amyotrophic lateral sclerosis, congestive obstructive pulmonary disease, cancer, AIDS, renal failure, organ atrophy, androgen deprivation, and rheumatoid arthritis.

Over-expression of myostatin may contribute to cachexia, a severe muscle and fat wasting syndrome. In one example, serum and intramuscular concentrations of myostatin-immunoreactive protein was found to be increased in men exhibiting AIDS-related muscle wasting and was inversely related to fat-free mass (Gonzalez-Cadavid et al., PNAS USA 95: 14938-14943 (1998)). Myostatin levels have also been shown to increase in response to burns injuries, resulting in a catabolic muscle effect (Lang et al, FASEB J 15, 1807-1809 (2001)). Additional conditions resulting in muscle wasting may arise from inactivity due to disability such as confinement in a wheelchair, prolonged bed rest due to stroke, illness, spinal chord injury, bone fracture or trauma, and muscular atrophy in a microgravity environment (space flight). For example, plasma myostatin immunoreactive protein was found to increase after prolonged bed rest (Zachwieja et al. J Gravit Physiol. 6(2): 11(1999). It was also found that the muscles of rats exposed to a microgravity environment during a space shuttle flight expressed an increased amount of myostatin compared with the muscles of rats which were not exposed (Lalani et al., J. Endocrin 167 (3):417-28 (2000)).

In addition, age-related increases in fat to muscle ratios, and age-related muscular atrophy appear to be related to myostatin. For example, the average serum myostatin-immunoreactive protein increased with age in groups of young (19-35 yr old), middle-aged (36-75 yr old), and elderly (76-92 yr old) men and women, while the average muscle mass and fat-free mass declined with age in these groups (Yarasheski et al. J Nutr Aging 6(5):343-8 (2002)). In addition, myostatin has now been found to be expressed at low levels in heart muscle and expression is upregulated after cardiomyocytes after infarct (Sharma et al., J Cell Physiol. 180 (1): 1-9 (1999)). Therefore, reducing myostatin levels in the heart muscle may improve recovery of heart muscle after infarct.

Myostatin also appears to influence metabolic disorders including type 2 diabetes, noninsulin-dependent diabetes mellitus, hyperglycemia, and obesity. For example, lack of myostatin has been shown to improve the obese and diabetic phenotypes of two mouse models (Yen et al. supra). It has been shown in the Examples below that administering AAV-ActRIIB5 vectors increases the muscle to fat ratio in an animal, in particular for obese animal models. Therefore, decreasing fat composition by administering the compositions of the present invention will improve diabetes, obesity, and hyperglycemic conditions in animals. In addition the Examples below and FIG. 4B demonstrates that compositions containing ActRIIB5 may decrease food intake in obese individuals.

In addition, increasing muscle mass by reducing myostatin levels may improve bone strength and reduce osteoporosis and other degenerative bone diseases. It has been found, for example, that myostatin-deficient mice showed increased mineral content and density of the mouse humerus and increased mineral content of both trabecular and cortical bone at the regions where the muscles attach, as well as increased muscle mass (Hamrick et al. Calcif Tissue Int 71(1):63-8 (2002)). In addition, the ActRIIB compositions of the present invention can be used to treat the effects of androgen deprivation such as androgen deprivation therapy used for the treatment of prostate cancer.

The present invention also provides methods and compositions for increasing muscle mass in food animals by administering an effective dosage of the ActRIIB5 proteins to the animal. Since the mature C-terminal myostatin polypeptide is identical in all species tested, ActRIIB5 proteins would be expected to be effective for increasing muscle mass and reducing fat in any agriculturally important species including cattle, chicken, turkeys, and pigs.

The ActRIIB5 proteins and compositions of the present invention also antagonizes the activity of activin A. Activin A is known to be expressed in certain types of cancers, particularly gonadal tumors such as ovarian carcinomas, and to cause severe cachexia. (Ciprano et al. Endocrinol 141 (7):2319-27 (2000), Shou et al., Endocrinol 138 (11):5000-5 (1997); Coerver et al, Mol Endocrinol 10(5):534-43 (1996); Ito et al. British J Cancer 82(8): 1415-20 (2000), Lambert-Messerlian, et al, Gynecologic Oncology 74 91):93-7 (1999). Example 4 below shows that expression of activin A in the animal models results in a severe cachexia. Expression of the ActRIIB5/Fc in the animals counters that cachexia, as shown in Examples 5 and 6. Overexpression of myostatin is also thought to contribute to cachexia, as described above. Therefore the compositions can be used to treat conditions related to activin A overexpression, as well as myostatin overexpression, such as cachexia from certain cancers and the treatment of certain gonadal type tumors.

The compositions of the present invention may be used alone or in combination with other therapeutic agents to enhance their therapeutic effects or decrease potential side effects. These properties include increased activity, increased solubility, reduced degradation, increased half-life, reduced toxicity, and reduced immunogenicity. Thus the compositions of the present invention are useful for extended treatment regimes. In addition, the properties of hydrophilicity and hydrophobicity of the compounds of the invention are well balanced, thereby enhancing their utility for both in vitro and especially in vivo uses. Specifically, compounds of the invention have an appropriate degree of solubility in aqueous media that permits absorption and bioavailability in the body, while also having a degree of solubility in lipids that permits the compounds to traverse the cell membrane to a putative site of action, such as a particular muscle mass.

In addition, the ActRIIB5 proteins and polypeptides of the present invention are useful for detecting and quantitating myostatin, activin A, or GDF-11 in any number of assays. In general, the ActRIIB5 polypeptides of the present invention are useful as capture agents to bind and immobilize myostatin, activin A, or GDF-11 in a variety of assays, similar to those described, for example, in Asai, ed., Methods in Cell Biology, 37, *Antibodies in Cell Biology*, Academic Press, Inc., New York (1993). The polypeptides may be labeled in some manner or may react with a third molecule such as an antibody which is labeled to enable myostatin to be detected and quantitated. For example, a polypeptide or a third molecule can be modified with a detectable moiety, such as biotin, which can then be bound by a fourth molecule, such as enzyme-labeled streptavidin, or other proteins. (Akerstrom, *J Immunol* 135:2589 (1985); Chaubert, *Mod Pathol* 10:585 (1997)).

The invention having been described, the following examples are offered by way of illustration, and not limitation.

EXAMPLE I

Isolation of cDNA and Expression in Cells

The cDNA of the novel human activin type IIB receptor was isolated from a cDNA library of human testis origin (Clontech, Inc.) according to the following protocol. Primers for the N-terminal and the C-terminal of the human activin IIB receptor (SEQ ID NO: 4) were generated and PCR was performed using these primers against templates from human cDNA libraries. PCT was performed using the GC-RICH PCR System (Roche, cat #2140306). Both N and C terminal PCR products were digested with PvuII/EcoRI and subcloned into pcDNA3.1-HisA vector (Invitrogen, Carlsbad, Calif.) to make a full length clone. After sequencing a number of PCR products, a cDNA clone from the human testes cDNA library was identified as a novel N-terminal splice variant receptor. The polynucleotide sequence of this receptor, designated human activin type IIB5 receptor (ActRIIB5). The cDNA clone of this receptor was missing 152 nucleotide bases that correspond to the entire Exon-4 in the wild-type human activin type IIB receptor gene. The truncation of exon-4 in the splice variant resulted in the deletion of the amino acid sequence that spans the transmembrane region as well as in a frame shift leading to an early translational termination. The amino acid sequence of the splice variant receptor contains most of the extracellular domain, encoded by exons 1, 2 and 3 of the wild-type human activin type IIB receptor, and an additional tail region of 36 amino acids resulting from the frame shift. The amino acid sequence is set forth in SEQ ID NO: 2. The C terminal sequence is set forth in SEQ ID NO: 3. Due to the lack of transmembrane region, the ActRIIB5 encodes a soluble form of activin type IIB receptor. Transfection of the ActRBII5 cDNA in cells led to the expression of secreted, instead of membrane-bound, form of the receptor protein.

EXAMPLE 2

Expression of ActRIIB5 cDNA encoding ActRIIB5 was cloned into a mammalian pDC323 or pDC324 vectors (Bianchi et al, Biotech and Bioengineering, Vol. 84(4):439-444 (2003)) and expressed in a 293T cell line. To generate the Fc fusions, polynucleotides encoding the ActRIIB5 (SEQ ID NO: 1) were cloned adjacent to polynucleotides encoding the $(Gly)_8$ linker sequence adjacent to polynucleotides encoding the human IgG1 Fc into a pDSRa vector (described in WO/9014363, herein incorporated by reference). Polynucleotides encoding ActRIIB-ECD (amino acids 1-124 of SEQ ID NO: 5) were cloned adjacent to polynucleotides encoding the human IgG1 Fc into a pDSRa vector (no linker). These constructs were transfected into a stable CHO cell line. The soluble receptor-Fc fusions expressed were used for the side-by-side in vitro testing described below.

For the in vivo animal experiments described in Example 4 below, the PCR products generated as described above were digested with NheI/SalI and subcloned into an AAV-Fc vector at the same sites. The AAV-Fc vector allows for transfer of the ActRIIB5 gene into an animal for expression in vivo.

EXAMPLE 3

In Vitro Activities

HuActRIIB5/Fc and HuActRIIB-ECD/Fc were generated as described above. The ability the ActRIIB5 receptor to inhibit the binding of each of the three ligands myostatin, activin A, and GDF-11 to the activin IIB receptor was tested using a cell based activity assay as described below.

C2C12 Cell Based Activity Assay

A myostatin/activin/GDF-11-responsive reporter cell line was generated by transfection of C2C12 myoblast cells (ATCC No: CRL-1772) with a pMARE-luc construct. The pMARE-luc construct was made by cloning twelve repeats of the CAGA sequence, representing the myostatin/activin response elements (Dennler et al. EMBO 17: 3091-3100 (1998)) into a pLuc-MCS reporter vector (Stratagene cat #219087) upstream of the TATA box. The myoblast C2C12 cells naturally express myostatin/activin/GDF-11 receptor activin receptor IIB on its cell surface. When myostatin/activinA/GDF-11 binds the cell receptors, the Smad pathway is activated, and phosphorylated Smad binds to the response element (Macias-Silva et al. Cell 87:1215 (1996)), resulting in the expression of the luciferase gene. Luciferase activity is then measured using a commercial luciferase reporter assay kit (cat #E4550, Promega, Madison, Wis.) according to manufacturer's protocol. A stable line of C2C12 cells that had been transfected with pMARE-luc (C2C12/pMARE clone #44) was used to measure activity according to the following procedure. Reporter cells were plated into 96 well cultures. Screening using dilutions of each type of soluble receptor was performed with the concentration fixed at 4 nM myostatin, 20 nM activin, and 4 nM GDF-11. Myostatin, activin and GDF-11 were each pre-incubated with the soluble receptors at several concentrations. Myostatin/activin/GDF-11 activity was measured by determining the luciferase activity in the treated cultures. The $IC_{50}$ values were for the determined for each soluble receptor as set out in Table 1 below.

TABLE 1

| Soluble receptor protein | activin A neutralizing activity IC50 (nM) vs. 20 nM activin |
|---|---|
| huActRIIB5/Fc | 156.2 |
| huActRIIB-ECD/Fc | 339.6 |

| soluble receptor protein | myostatin-neutralizing activity IC50 (nM) vs. 4 nM myostatin |
|---|---|
| huActRIIB5/Fc | 29.72 |
| huActRIIB-ECD/Fc | 51.06 |

| soluble receptor protein | GDF-11-neutralizing activity IC50(nM) vs. 4 nM GDF-11 |
|---|---|
| huACtRIIB5/Fc | 90.6 |
| huActRIIB-ECD/Fc | 89.88 |

The table above shows that the soluble receptors can block myostatin signaling through its receptor but also activin A and GDF-11 signaling.

BIAcore® Assay

Blocking assays were carried out using immobilized human ActRIIB-ECD/Fc (R&D Systems, Minneapolis, Mn.) on a CM5 chip (Biacore, Inc., Piscataway, N.J.) in the presence and absence of each of the two soluble receptors ActRIIB-ECD/Fc and ActRIIB5/Fc using the BIAcore® assay system according to the manufacturer's instructions. 100% myostatin binding signal was determined in the absence of receptor in solution. Various concentrations of the soluble receptors were diluted in sample buffer and incubated with 4 nM myostatin before being injected over the receptor surface. Since only free myostatin molecules were able to bind to the chip, a decreased binding response with increasing concentration of the receptors indicated binding of the receptors to myostatin in solution. Plotting the binding signal vs. concentration of soluble receptor, ActRIIB-ECD/Fc and ActRIIB5/Fc were calculated to have an $EC_{50}$ of approximately 18 nM and 7 nM respectively. The comparison between the two receptors is shown in FIG. 1.

EXAMPLE 4

Activin A Over-Expression in C57Bl/6 Mice

To explore the postnatal role of activin in postnatal animals, activin A was overexpressed in mice using AAV mediated gene transfer. Aged-matched young adult (5-week-old) female C57Bl/6 mice (Charles River laboratories, Wilmington, Mass.) were separated into two weight-balanced groups (n=6/group), which were subsequently injected via portal vein with either AAV-activin A or AAV-empty vector (control) at $1 \times 10^{13}$ pfu/mouse. The effects on body weight and body composition were analyzed. AAV-activin A transduced group showed a drastic reduction in body weight compared to the control mice transduced with AAV-empty vector. Within 2 weeks post AAV injection, the activin A-transduced group became so severely cachectic that their average body weight was only about ½ of that of empty vector-transduced control group. Necropsy revealed that AAV-activin A administration resulted a dramatic depletion by approximately 60% of lean body mass, skeletal muscle mass and fat mass. In addition, the activin-transduced mice also showed severe wasting of organs as indicated by significantly reduced organ weights such as liver and heart.

An additional experiment using a reduced amount ($1 \times 10^{12}$ pfu/mouse) of AAV-Activin A virus was performed. The results showed a reduction in body weight and lean body mass resulting from activin-transduction but the effects were less dramatic as compared to the initial experiment using AAV-activin A at a higher dose ($1 \times 10^{13}$ pfu/mouse). This demonstrates that the postnatal cachectic effect of activin A is dose-dependent.

EXAMPLE 5

Anabolic Effect of AAV-ActRIIB5 in C57Bl/6 Mice

Figure 2:
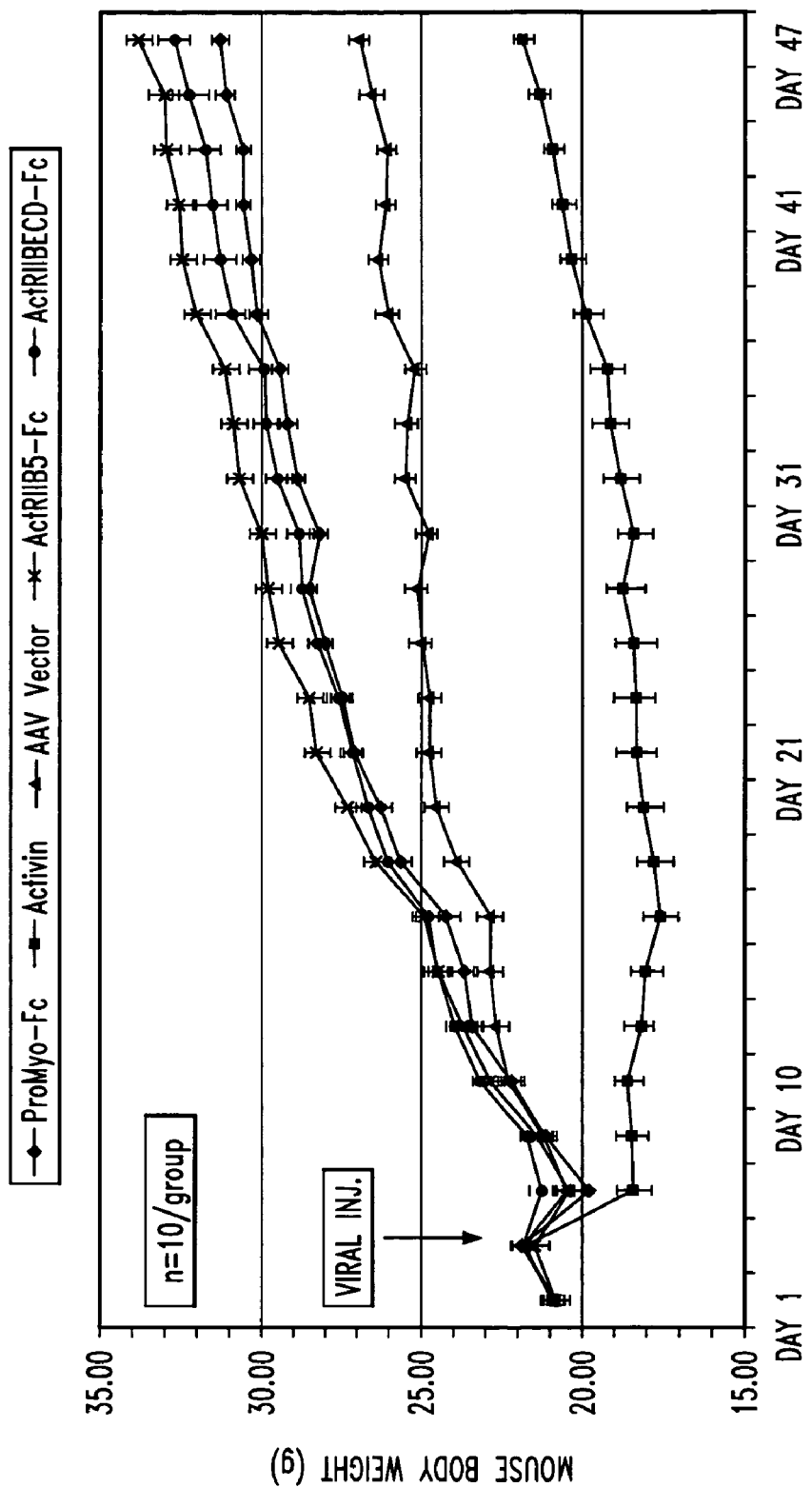
FIG. 2 shows the increase in body weight over time in C57Bl/6 mice injected with AAV-activin A, AAV-promyostatin/Fc, AAV-ActRIIB5/Fc, AAV-ActRIIB-ECD/Fc and AAV-empty vector control.

Age-matched (5-week-old) C57Bl/6 male mice were divided into 5 groups (n=10 per group). AAV viral particles were packaged and titered prior to injection as follows: AAV-empty, AAV-activin A, AAV-ActRIIB5/Fc, AAV-ActRIIB-ECD/Fc, and AAV-ProMyo/Fc, wherein AAV-ProMyo stands for propeptide of myostatin. Each of the above AAV viruses were injected at $8 \times 10^{12}$ pfu/mouse except for AAV-activin A, of which an reduced amount of viral particles at $1 \times 10^{12}$ pfu/mouse was injected (n=10/group). The viral particles were injected via the portal vein. Body weights were determined every other day. The results are shown in FIG. 2. AAV-ActRIIB5/Fc group and the AAV-ActRIIB-ECD/Fc group developed increased body weights compared to the AAV-Vector control group, as well as increased body weight compared to the AAV-ProMyo/Fc group. Comparing the two soluble receptor groups, the AAV-ActRIIB5/Fc group showed the greatest amount of increase in body weight gain. In contrast, the AAV-Vector control group showed a dramatic decrease in body weights in comparison to the AAV-Vector control group.

Figure 3:
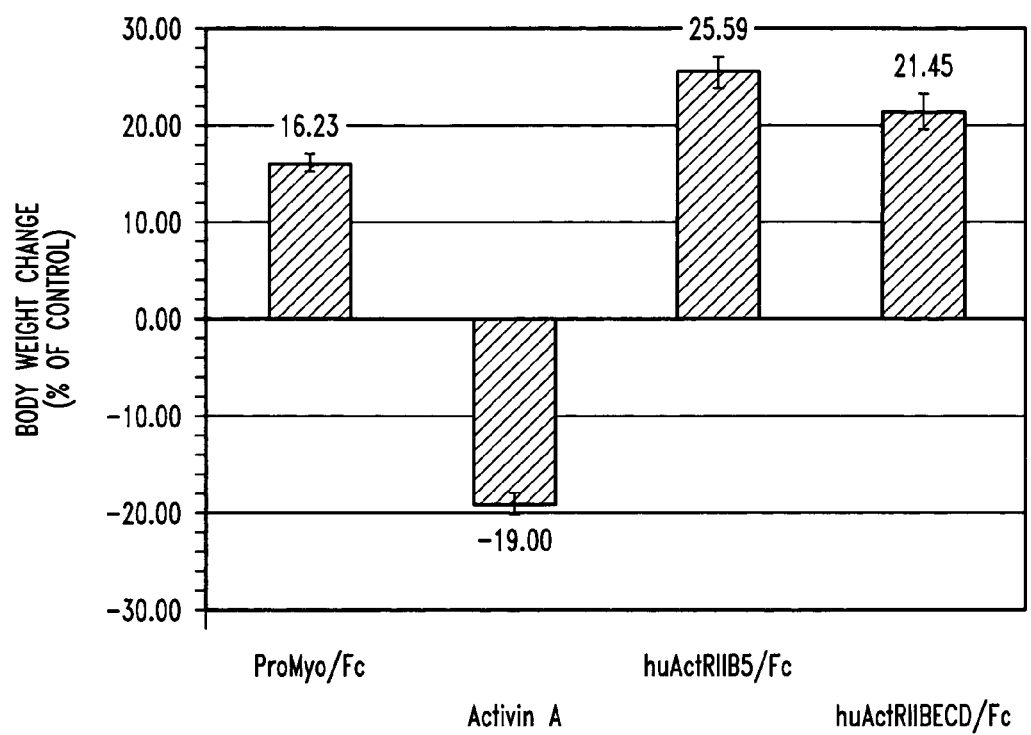
FIG. 3 shows the percentage of body weight change compared to the control at seven weeks post viral infection in C57Bl/6 mice injected with AAV-activin A, AAV-ActRIIB5/Fc, AAV-ActRIIB-ECD/Fc, and AAV-promyostatin/Fc vector.

At seven weeks post viral injection, body weight changes of individual groups were plotted as percentage of that of the control group (AAV-empty vector group). The AAV-ActRIIB5/Fc group showed the highest average body weight increase over control, approximately 25%, compared with 21% body weight increase for the ActRIIB-ECD/Fc group. The AAV-ActRIIB5/Fc group and the AAV-ActRIIB-ECD/Fc group showed body weight increases greater than that elicited by the ProMyo/Fc group of approximately 16%. In contrast, AAV-activin group had a significant drop in body weight by 19%. A comparison of these changes is shown in FIG. 3.

One-month post viral injection, lean body mass in each group of ten mice was determined using nuclear magnetic resonance (NMR) by measuring body composition of live mice. At the same time, the body fat content of the mice in each group was determined. The measurements were taken on live mice using the EchoMRI 2003 (Echo Medical Systems, Houston, Tex.). EchoMRI 2004 is a whole body composition analyzer that measures the masses of fat and lean tissues in live animals using NMR technology. The average percentage of lean mass and fat as percentage of body weight for each group of 10 mice is presented in Table 2 below.

TABLE 2

|  | Fat (% body weight) | lean mass (% body weight) |
| --- | --- | --- |
| AAV-promyostatin/Fc | 9.11 | 90.33 |
| AAV-Activin A | 10.21 | 87.92 |
| AAV-empty | 11.76 | 86.74 |
| AAV-ActRIIB5/Fc | 7.82 | 91.05 |
| AAV-ActRIIB-ECD/Fc | 8.51 | 90.18 |

As can be seen from Table 2 above, the AAV-ActRIIB5/Fc group of mice showed the smallest percentage of body fat, and the largest percentage of lean mass for all of the groups after one month. This data shows that ActRIIB5/Fc is effective in enhancing body weight, lean body mass and decreasing fat mass in the animals tested.

In a related experiment, the five groups of ten mice per group were tested for gripping strength using a Columbia Instruments meter, model 1027 dsm (Columbus, Ohio). The results were averaged for each group. The AAV-promyostatin/Fc group averaged a gripping strength compared with the AAV-empty control mice was about 21% for the promyostatin/Fc group, about 31% for the ActRIIB-ECD/Fc group and about 33% for the ActRIIB5/Fc group of mice. The increase in gripping strength measured was about 46% for the promyostatin/Fc group, about 56% for the ActRIIB-ECD/Fc group, and about 60% for the ActRIIB5/Fc group.

EXAMPLE VI

Changes in Body Weight and Composition in Ay Obese Mice

Two groups of Ay Obese mice (Jackson Laboratories, Bar Harbor, Me.) of 11 animals each (8 animals per group at the termination of the experiment) were injected with an AAV-empty vector and an AAV-ActRIIB5/Fc vector respectively. The viruses were injected at $8 \times 10^{12}$ pfu/mouse into the portal vein of each mouse. The mice were then monitored for changes in body weight, food intake, lean muscle mass and fat mass over a three month period post injection. Food intake was determined by weighing the remaining uneaten food in the mouse cage on a daily basis and calculating the weekly intake. The lean muscle mass and fat mass were determined by NMR as described above. The results of the experiments are shown in FIGS. 4 and 5. FIG. 4A shows a decrease in body weight and FIG. 4B shows a decrease in weekly food intake in the AAV-ActRIIB5/Fc mice compared with the control mice. FIG. 5A shows increase in lean mass, as determined by NMR for the AAV-ActRIIB5/Fc, while FIG. 5B shows a large decrease of fat mass for the AAV-ActRIIB/Fc compared to the control mice, by approximately 50%.

At the termination of the experiment, the mice were sacrificed and examined for internal changes. The livers of the AAV-ActRIIB5/Fc treated mice were compared with those treated with AAV-empty control. Visual inspection of the livers of the AAV-empty treated mice and the AAV-ActRIIB5/Fc treated mice showed that the livers of the control AAV-empty mice contained fat deposits within the livers, whereas the AAV-ActRIIB5/Fc treated mice were free of fat deposits. Therefore, the expression of the ActRIIB5/Fc in the Ay mice corrected the fatty livers which characterize the Ay obese mice, as well as caused a decrease in overall body weight, a decrease in amount of food consumed, an increase in lean muscle mass and large decrease in fat mass.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. An isolated nucleic acid molecule comprising a polynucleotide selected from the group consisting of:
   (a) a polynucleotide consisting of the sequence set forth in SEQ ID NO: 1;
   (b) a polynucleotide encoding a polypeptide consisting of the amino acid sequence set forth in SEQ ID NO: 2; and
   (c) a polynucleotide encoding a polypeptide consisting of an amino acid sequence at least 95% identical to SEQ ID NO: 2, wherein the polypeptide is capable of binding myostatin, activin A or GDF-11.

2. The isolated nucleic acid molecule of claim 1, wherein the nucleic acid molecule further comprises polynucleotides encoding at least one heterologous protein in frame with the polynucleotides set forth in claim 1.

3. The isolated nucleic acid molecule of claim 2, wherein heterologous protein is an Fc polypeptide.

4. The isolated nucleic acid molecule of claim 3, wherein the Fc polypeptide is attached by a linker peptide.

5. A recombinant vector that directs the expression of the nucleic acid molecule of claim 1.

6. An isolated host cell comprising the recombinant vector of claim 5.

7. The host cell of claim 6 wherein the host cell is a mammalian cell.

8. A method of producing an activin IIB5 receptor polypeptide comprising culturing the host cell of claim 6 under conditions promoting expression of the polypeptide, and recovering the polypeptide.

9. An isolated nucleic acid molecule comprising a polynucleotide consisting of the sequence set forth in SEQ ID NO: 1.

10. The nucleic acid molecule of any one of claims 1 and 2 through 9, wherein the polynucleotide is operably linked to a transcriptional or translational regulatory sequence.

11. The nucleic acid molecule of claim 10 wherein the transcriptional or translational sequence comprises a transcriptional promoter or enhancer.

* * * * *

SEQUENCE LISTING

<160> NUMBER OF SEQ ID NOS: 6

<210> SEQ ID NO 1
<211> LENGTH: 1387
<212> TYPE: DNA
<213> ORGANISM: Homo sapiens
<220> FEATURE:
<221> NAME/KEY: CDS

<222> LOCATION: (1)..(480)

<400> SEQUENCE: 1

| | | | | | | | | | | | | | | | | |
|---|---|---|---|---|---|---|---|---|---|---|---|---|---|---|---|---|
| atg | acg | gcg | ccc | tgg | gtg | gcc | ctc | gcc | ctc | ctc | tgg | gga | tcg | ctg | tgc | 48 |
| Met | Thr | Ala | Pro | Trp | Val | Ala | Leu | Ala | Leu | Leu | Trp | Gly | Ser | Leu | Cys | |
| 1 | | | | 5 | | | | | 10 | | | | | 15 | | |
| gcc | ggc | tct | ggg | cgt | ggg | gag | gct | gag | aca | cgg | gag | tgc | atc | tac | tac | 96 |
| Ala | Gly | Ser | Gly | Arg | Gly | Glu | Ala | Glu | Thr | Arg | Glu | Cys | Ile | Tyr | Tyr | |
| | | | 20 | | | | | 25 | | | | | 30 | | | |
| aac | gcc | aac | tgg | gag | ctg | gag | cgc | acc | aac | cag | agc | ggc | ctg | gag | cgc | 144 |
| Asn | Ala | Asn | Trp | Glu | Leu | Glu | Arg | Thr | Asn | Gln | Ser | Gly | Leu | Glu | Arg | |
| | 35 | | | | | 40 | | | | | 45 | | | | | |
| tgc | gaa | ggc | gag | cag | gac | aag | cgg | ctg | cac | tgc | tac | gcc | tcc | tgg | cgc | 192 |
| Cys | Glu | Gly | Glu | Gln | Asp | Lys | Arg | Leu | His | Cys | Tyr | Ala | Ser | Trp | Arg | |
| 50 | | | | | 55 | | | | | 60 | | | | | | |
| aac | agc | tct | ggc | acc | atc | gag | ctc | gtg | aag | aag | ggc | tgc | tgg | cta | gat | 240 |
| Asn | Ser | Ser | Gly | Thr | Ile | Glu | Leu | Val | Lys | Lys | Gly | Cys | Trp | Leu | Asp | |
| 65 | | | | 70 | | | | | 75 | | | | | 80 | | |
| gac | ttc | aac | tgc | tac | gat | agg | cag | gag | tgt | gtg | gcc | act | gag | gag | aac | 288 |
| Asp | Phe | Asn | Cys | Tyr | Asp | Arg | Gln | Glu | Cys | Val | Ala | Thr | Glu | Glu | Asn | |
| | | 85 | | | | | 90 | | | | | 95 | | | | |
| ccc | cag | gtg | tac | ttc | tgc | tgt | gaa | ggc | aac | ttc | tgc | aac | gag | cgc | | 336 |
| Pro | Gln | Val | Tyr | Phe | Cys | Cys | Glu | Gly | Asn | Phe | Cys | Asn | Glu | Arg | | |
| | | | 100 | | | | | 105 | | | | | 110 | | | |
| ttc | act | cat | ttg | cca | gag | gct | ggg | ggc | ccg | gaa | gga | ccc | tgg | gcc | tcc | 384 |
| Phe | Thr | His | Leu | Pro | Glu | Ala | Gly | Gly | Pro | Glu | Gly | Pro | Trp | Ala | Ser | |
| | | 115 | | | | | 120 | | | | | 125 | | | | |
| acc | acc | atc | ccc | tct | ggt | ggg | cct | gaa | gcc | act | gca | gct | gct | gga | gat | 432 |
| Thr | Thr | Ile | Pro | Ser | Gly | Gly | Pro | Glu | Ala | Thr | Ala | Ala | Ala | Gly | Asp | |
| | 130 | | | | | 135 | | | | | 140 | | | | | |
| caa | ggc | tcg | ggg | gcg | ctt | tgg | ctg | tgt | ctg | gaa | ggc | cca | gct | cat | gaa | 480 |
| Gln | Gly | Ser | Gly | Ala | Leu | Trp | Leu | Cys | Leu | Glu | Gly | Pro | Ala | His | Glu | |
| 145 | | | | | 150 | | | | | 155 | | | | | 160 | |

| | |
|---|---|
| tgactttgta gctgtcaaga tcttcccact ccaggacaag cagtcgtggc agagtgaacg | 540 |
| ggagatcttc agcacacctg gcatgaagca cgagaacctg ctacagttca ttgctgccga | 600 |
| gaagcgaggc tccaacctcg aagtagagct gtggctcatc acggccttcc atgacaaggg | 660 |
| ctccctcacg gattacctca gggaacat catcacatgg aacgaactgt gtcatgtagc | 720 |
| agagacgatg tcacgaggcc tctcatacct gcatgaggat gtgccctggt gccgtggcga | 780 |
| gggccacaag ccgtctattg cccacaggga ctttaaaagt aagaatgtat tgctgaagag | 840 |
| cgacctcaca gccgtgctgg ctgactttgg cttggctgtt cgatttgagc agggaaaacc | 900 |
| tccagggac acccacggac aggtaggcac gagacggtac atggctcctg aggtgctcga | 960 |
| gggagccatc aacttccaga gagatgcctt cctgcgcatt gacatgtatg ccatggggtt | 1020 |
| ggtgctgtgg gagcttgtgt ctcgctgcaa ggctgcagac ggaccgtgg atgagtacat | 1080 |
| gctgcccttt gaggaagaga ttggccagca ccttcgttg gaggagctgc aggaggtggt | 1140 |
| ggtgcacaag aagatgaggc ccaccattaa agatcactgg ttgaaacacc cgggcctggc | 1200 |
| ccagctttgt gtgaccatcg aggagtgctg ggaccatgat gcagaggctc gcttgtccgc | 1260 |
| gggctgtgtg gaggagcggg tgtccctgat tcggaggtcg gtcaatggca ctacctcgga | 1320 |
| ctgtctcgtt tccctggtga cctctgtcac caatgtggac ctgccccta aagagtcaag | 1380 |
| catctaa | 1387 |

<210> SEQ ID NO 2
<211> LENGTH: 160
<212> TYPE: PRT

<213> ORGANISM: Homo sapiens

<400> SEQUENCE: 2

```
Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Gly Pro Trp Ala Ser
        115                 120                 125

Thr Thr Ile Pro Ser Gly Gly Pro Glu Ala Thr Ala Ala Ala Gly Asp
130                 135                 140

Gln Gly Ser Gly Ala Leu Trp Leu Cys Leu Glu Gly Pro Ala His Glu
145                 150                 155                 160
```

<210> SEQ ID NO 3
<211> LENGTH: 36
<212> TYPE: PRT
<213> ORGANISM: Homo sapiens

<400> SEQUENCE: 3

```
Pro Trp Ala Ser Thr Thr Ile Pro Ser Gly Gly Pro Glu Ala Thr Ala
1               5                   10                  15

Ala Ala Gly Asp Gln Gly Ser Gly Ala Leu Trp Leu Cys Leu Glu Gly
            20                  25                  30

Pro Ala His Glu
        35
```

<210> SEQ ID NO 4
<211> LENGTH: 1539
<212> TYPE: DNA
<213> ORGANISM: Homo sapiens
<220> FEATURE:
<221> NAME/KEY: CDS
<222> LOCATION: (1)..(1539)

<400> SEQUENCE: 4

```
atg acg gcg ccc tgg gtg gcc ctc gcc ctc ctc tgg gga tcg ctg tgc      48
Met Thr Ala Pro Trp Val Ala Leu Ala Leu Leu Trp Gly Ser Leu Cys
1               5                   10                  15 gcc ggc tct ggg cgt ggg gag gct gag aca cgg gag tgc atc tac tac      96
Ala Gly Ser Gly Arg Gly Glu Ala Glu Thr Arg Glu Cys Ile Tyr Tyr
            20                  25                  30 aac gcc aac tgg gag ctg gag cgc acc aac cag agc ggc ctg gag cgc     144
Asn Ala Asn Trp Glu Leu Glu Arg Thr Asn Gln Ser Gly Leu Glu Arg
        35                  40                  45 tgc gaa ggc gag cag gac aag cgg ctg cac tgc tac gcc tcc tgg cgc     192
Cys Glu Gly Glu Gln Asp Lys Arg Leu His Cys Tyr Ala Ser Trp Arg
50                  55                  60 aac agc tct ggc acc atc gag ctc gtg aag aag ggc tgc tgg cta gat     240
Asn Ser Ser Gly Thr Ile Glu Leu Val Lys Lys Gly Cys Trp Leu Asp
```

|     |     |     |     |     |     |     |     |     |     |     |     |     |     |     |     |     |
|---|---|---|---|---|---|---|---|---|---|---|---|---|---|---|---|---|
| 65 | | | | | 70 | | | | | 75 | | | | | 80 | |

| gac | ttc | aac | tgc | tac | gat | agg | cag | gag | tgt | gtg | gcc | act | gag | gag | aac | 288 |
| Asp | Phe | Asn | Cys | Tyr | Asp | Arg | Gln | Glu | Cys | Val | Ala | Thr | Glu | Glu | Asn | |
| | | | | 85 | | | | | 90 | | | | | 95 | | |

| ccc | cag | gtg | tac | ttc | tgc | tgt | gaa | ggc | aac | ttc | tgc | aac | gag | cgc | | 336 |
| Pro | Gln | Val | Tyr | Phe | Cys | Cys | Glu | Gly | Asn | Phe | Cys | Asn | Glu | Arg | | |
| | | 100 | | | | | 105 | | | | | 110 | | | | |

| ttc | act | cat | ttg | cca | gag | gct | ggg | ggc | ccg | gaa | gtc | acg | tac | gag | cca | 384 |
| Phe | Thr | His | Leu | Pro | Glu | Ala | Gly | Gly | Pro | Glu | Val | Thr | Tyr | Glu | Pro | |
| | | | 115 | | | | | 120 | | | | | 125 | | | |

| ccc | cca | aca | gcc | ccc | acc | ctg | ctc | acg | gtg | ctg | gcc | tac | tca | ctg | ctg | 432 |
| Pro | Pro | Thr | Ala | Pro | Thr | Leu | Leu | Thr | Val | Leu | Ala | Tyr | Ser | Leu | Leu | |
| | 130 | | | | | 135 | | | | | 140 | | | | | |

| ccc | atc | ggg | ggc | ctt | tcc | ctc | atc | gtc | ctg | ctg | gcc | ttt | tgg | atg | tac | 480 |
| Pro | Ile | Gly | Gly | Leu | Ser | Leu | Ile | Val | Leu | Leu | Ala | Phe | Trp | Met | Tyr | |
| 145 | | | | | 150 | | | | | 155 | | | | | 160 | |

| cgg | cat | cgc | aag | ccc | ccc | tac | ggt | cat | gtg | gac | atc | cat | gag | gac | cct | 528 |
| Arg | His | Arg | Lys | Pro | Pro | Tyr | Gly | His | Val | Asp | Ile | His | Glu | Asp | Pro | |
| | | | | 165 | | | | | 170 | | | | | 175 | | |

| ggg | cct | cca | cca | cca | tcc | cct | ctg | gtg | ggc | ctg | aag | cca | ctg | cag | ctg | 576 |
| Gly | Pro | Pro | Pro | Pro | Ser | Pro | Leu | Val | Gly | Leu | Lys | Pro | Leu | Gln | Leu | |
| | | | 180 | | | | | 185 | | | | | 190 | | | |

| ctg | gag | atc | aag | gct | cgg | ggg | cgc | ttt | ggc | tgt | gtc | tgg | aag | gcc | cag | 624 |
| Leu | Glu | Ile | Lys | Ala | Arg | Gly | Arg | Phe | Gly | Cys | Val | Trp | Lys | Ala | Gln | |
| | | 195 | | | | | 200 | | | | | 205 | | | | |

| ctc | atg | aat | gac | ttt | gta | gct | gtc | aag | atc | ttc | cca | ctc | cag | gac | aag | 672 |
| Leu | Met | Asn | Asp | Phe | Val | Ala | Val | Lys | Ile | Phe | Pro | Leu | Gln | Asp | Lys | |
| | 210 | | | | | 215 | | | | | 220 | | | | | |

| cag | tcg | tgg | cag | agt | gaa | cgg | gag | atc | ttc | agc | aca | cct | ggc | atg | aag | 720 |
| Gln | Ser | Trp | Gln | Ser | Glu | Arg | Glu | Ile | Phe | Ser | Thr | Pro | Gly | Met | Lys | |
| 225 | | | | | 230 | | | | | 235 | | | | | 240 | |

| cac | gag | aac | ctg | cta | cag | ttc | att | gct | gcc | gag | aag | cga | ggc | tcc | aac | 768 |
| His | Glu | Asn | Leu | Leu | Gln | Phe | Ile | Ala | Ala | Glu | Lys | Arg | Gly | Ser | Asn | |
| | | | | 245 | | | | | 250 | | | | | 255 | | |

| ctc | gaa | gta | gag | ctg | tgg | ctc | atc | acg | gcc | ttc | cat | gac | aag | ggc | tcc | 816 |
| Leu | Glu | Val | Glu | Leu | Trp | Leu | Ile | Thr | Ala | Phe | His | Asp | Lys | Gly | Ser | |
| | | | 260 | | | | | 265 | | | | | 270 | | | |

| ctc | acg | gat | tac | ctc | aag | ggg | aac | atc | atc | aca | tgg | aac | gaa | ctg | tgt | 864 |
| Leu | Thr | Asp | Tyr | Leu | Lys | Gly | Asn | Ile | Ile | Thr | Trp | Asn | Glu | Leu | Cys | |
| | | 275 | | | | | 280 | | | | | 285 | | | | |

| cat | gta | gca | gag | acg | atg | tca | cga | ggc | ctc | tca | tac | ctg | cat | gag | gat | 912 |
| His | Val | Ala | Glu | Thr | Met | Ser | Arg | Gly | Leu | Ser | Tyr | Leu | His | Glu | Asp | |
| | 290 | | | | | 295 | | | | | 300 | | | | | |

| gtg | ccc | tgg | tgc | cgt | ggc | gag | ggc | cac | aag | ccg | tct | att | gcc | cac | agg | 960 |
| Val | Pro | Trp | Cys | Arg | Gly | Glu | Gly | His | Lys | Pro | Ser | Ile | Ala | His | Arg | |
| 305 | | | | | 310 | | | | | 315 | | | | | 320 | |

| gac | ttt | aaa | agt | aag | aat | gta | ttg | ctg | aag | agc | gac | ctc | aca | gcc | gtg | 1008 |
| Asp | Phe | Lys | Ser | Lys | Asn | Val | Leu | Leu | Lys | Ser | Asp | Leu | Thr | Ala | Val | |
| | | | | 325 | | | | | 330 | | | | | 335 | | |

| ctg | gct | gac | ttt | ggc | ttg | gct | gtt | cga | ttt | gag | cca | ggg | aaa | cct | cca | 1056 |
| Leu | Ala | Asp | Phe | Gly | Leu | Ala | Val | Arg | Phe | Glu | Pro | Gly | Lys | Pro | Pro | |
| | | | 340 | | | | | 345 | | | | | 350 | | | |

| ggg | gac | acc | cac | gga | cag | gta | ggc | acg | aga | cgg | tac | atg | gct | cct | gag | 1104 |
| Gly | Asp | Thr | His | Gly | Gln | Val | Gly | Thr | Arg | Arg | Tyr | Met | Ala | Pro | Glu | |
| | | | 355 | | | | | 360 | | | | | 365 | | | |

| gtg | ctc | gag | gga | gcc | atc | aac | ttc | cag | aga | gat | gcc | ttc | ctg | cgc | att | 1152 |
| Val | Leu | Glu | Gly | Ala | Ile | Asn | Phe | Gln | Arg | Asp | Ala | Phe | Leu | Arg | Ile | |
| | 370 | | | | | 375 | | | | | 380 | | | | | |

| gac | atg | tat | gcc | atg | ggg | ttg | gtg | ctg | tgg | gag | ctt | gtg | tct | cgc | tgc | 1200 |
| Asp | Met | Tyr | Ala | Met | Gly | Leu | Val | Leu | Trp | Glu | Leu | Val | Ser | Arg | Cys | |

```
                385                 390                 395                 400
aag gct gca gac gga ccc gtg gat gag tac atg ctg ccc ttt gag gaa       1248
Lys Ala Ala Asp Gly Pro Val Asp Glu Tyr Met Leu Pro Phe Glu Glu
                    405                 410                 415 gag att ggc cag cac cct tcg ttg gag gag ctg cag gag gtg gtg gtg       1296
Glu Ile Gly Gln His Pro Ser Leu Glu Glu Leu Gln Glu Val Val Val
                420                 425                 430 cac aag aag atg agg ccc acc att aaa gat cac tgg ttg aaa cac ccg       1344
His Lys Lys Met Arg Pro Thr Ile Lys Asp His Trp Leu Lys His Pro
            435                 440                 445 ggc ctg gcc cag ctt tgt gtg acc atc gag gag tgc tgg gac cat gat       1392
Gly Leu Ala Gln Leu Cys Val Thr Ile Glu Glu Cys Trp Asp His Asp
        450                 455                 460 gca gag gct cgc ttg tcc gcg ggc tgt gtg gag gag cgg gtg tcc ctg       1440
Ala Glu Ala Arg Leu Ser Ala Gly Cys Val Glu Glu Arg Val Ser Leu
465                 470                 475                 480 att cgg agg tcg gtc aat ggc act acc tcg gac tgt ctc gtt tcc ctg       1488
Ile Arg Arg Ser Val Asn Gly Thr Thr Ser Asp Cys Leu Val Ser Leu
                    485                 490                 495 gtg acc tct gtc acc aat gtg gac ctg ccc cct aaa gag tca agc atc       1536
Val Thr Ser Val Thr Asn Val Asp Leu Pro Pro Lys Glu Ser Ser Ile
                500                 505                 510 taa                                                                   1539

<210> SEQ ID NO 5
<211> LENGTH: 512
<212> TYPE: PRT
<213> ORGANISM: Homo sapiens

<400> SEQUENCE: 5

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
            20                  25                  30

Asn Ala Asn Trp Glu Leu Glu Arg Thr Asn Gln Ser Gly Leu Glu Arg
        35                  40                  45

Cys Glu Gly Glu Gln Asp Lys Arg Leu His Cys Tyr Ala Ser Trp Arg
    50                  55                  60

Asn Ser Ser Gly Thr Ile Glu Leu Val Lys Lys Gly Cys Trp Leu Asp
65                  70                  75                  80

Asp Phe Asn Cys Tyr Asp Arg Gln Glu Cys Val Ala Thr Glu Glu Asn
                85                  90                  95

Pro Gln Val Tyr Phe Cys Cys Cys Glu Gly Asn Phe Cys Asn Glu Arg
            100                 105                 110

Phe Thr His Leu Pro Glu Ala Gly Gly Pro Glu Val Thr Tyr Glu Pro
        115                 120                 125

Pro Pro Thr Ala Pro Thr Leu Leu Thr Val Leu Ala Tyr Ser Leu Leu
    130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Pro Ser Pro Leu Val Gly Leu Lys Pro Leu Gln Leu
            180                 185                 190

Leu Glu Ile Lys Ala Arg Gly Arg Phe Gly Cys Val Trp Lys Ala Gln
        195                 200                 205

Leu Met Asn Asp Phe Val Ala Val Lys Ile Phe Pro Leu Gln Asp Lys
```

```
            210                 215                 220
Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
                260                 265                 270

Leu Thr Asp Tyr Leu Lys Gly Asn Ile Ile Thr Trp Asn Glu Leu Cys
                275                 280                 285

His Val Ala Glu Thr Met Ser Arg Gly Leu Ser Tyr Leu His Glu Asp
                290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
                340                 345                 350

Gly Asp Thr His Gly Gln Val Gly Thr Arg Arg Tyr Met Ala Pro Glu
                355                 360                 365

Val Leu Glu Gly Ala Ile Asn Phe Gln Arg Asp Ala Phe Leu Arg Ile
                370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
                420                 425                 430

His Lys Lys Met Arg Pro Thr Ile Lys Asp His Trp Leu Lys His Pro
                435                 440                 445

Gly Leu Ala Gln Leu Cys Val Thr Ile Glu Glu Cys Trp Asp His Asp
                450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
                500                 505                 510

<210> SEQ ID NO 6
<211> LENGTH: 512
<212> TYPE: PRT
<213> ORGANISM: Homo sapiens

<400> SEQUENCE: 6

Met Thr Ala Pro Trp Val Ala Leu Ala Leu Leu Trp Gly Ser Leu Cys
1               5                   10                  15

Ala Gly Ser Gly Arg Gly Glu Ala Glu Thr Arg Glu Cys Ile Tyr Tyr
                20                  25                  30

Asn Ala Asn Trp Glu Leu Glu Arg Thr Asn Gln Ser Gly Leu Glu Arg
                35                  40                  45

Cys Glu Gly Glu Gln Asp Lys Arg Leu His Cys Tyr Ala Ser Trp Ala
                50                  55                  60

Asn Ser Ser Gly Thr Ile Glu Leu Val Lys Lys Gly Cys Trp Leu Asp
65              70                  75                  80

Asp Phe Asn Cys Tyr Asp Arg Gln Glu Cys Val Ala Thr Glu Glu Asn
```

```
                   85                  90                  95
Pro Gln Val Tyr Phe Cys Cys Cys Glu Gly Asn Phe Cys Asn Glu Arg
                100                 105                 110

Phe Thr His Leu Pro Glu Ala Gly Gly Pro Glu Val Thr Tyr Glu Pro
                115                 120                 125

Pro Pro Thr Ala Pro Thr Leu Leu Thr Val Leu Ala Tyr Ser Leu Leu
                130                 135                 140

Pro Ile Gly Gly Leu Ser Leu Ile Val Leu Leu Ala Phe Trp Met Tyr
145                 150                 155                 160

Arg His Arg Lys Pro Pro Tyr Gly His Val Asp Ile His Glu Asp Pro
                165                 170                 175

Gly Pro Pro Pro Ser Pro Leu Val Gly Leu Lys Pro Leu Gln Leu
                180                 185                 190

Leu Glu Ile Lys Ala Arg Gly Arg Phe Gly Cys Val Trp Lys Ala Gln
                195                 200                 205

Leu Met Asn Asp Phe Val Ala Val Lys Ile Phe Pro Leu Gln Asp Lys
                210                 215                 220

Gln Ser Trp Gln Ser Glu Arg Glu Ile Phe Ser Thr Pro Gly Met Lys
225                 230                 235                 240

His Glu Asn Leu Leu Gln Phe Ile Ala Ala Glu Lys Arg Gly Ser Asn
                245                 250                 255

Leu Glu Val Glu Leu Trp Leu Ile Thr Ala Phe His Asp Lys Gly Ser
                260                 265                 270

Leu Thr Asp Tyr Leu Lys Gly Asn Ile Ile Thr Trp Asn Glu Leu Cys
                275                 280                 285

His Val Ala Glu Thr Met Ser Arg Gly Leu Ser Tyr Leu His Glu Asp
                290                 295                 300

Val Pro Trp Cys Arg Gly Glu Gly His Lys Pro Ser Ile Ala His Arg
305                 310                 315                 320

Asp Phe Lys Ser Lys Asn Val Leu Leu Lys Ser Asp Leu Thr Ala Val
                325                 330                 335

Leu Ala Asp Phe Gly Leu Ala Val Arg Phe Glu Pro Gly Lys Pro Pro
                340                 345                 350

Gly Asp Thr His Gly Gln Val Gly Thr Arg Arg Tyr Met Ala Pro Glu
                355                 360                 365

Val Leu Glu Gly Ala Ile Asn Phe Gln Arg Asp Ala Phe Leu Arg Ile
                370                 375                 380

Asp Met Tyr Ala Met Gly Leu Val Leu Trp Glu Leu Val Ser Arg Cys
385                 390                 395                 400

Lys Ala Ala Asp Gly Pro Val Asp Glu Tyr Met Leu Pro Phe Glu Glu
                405                 410                 415

Glu Ile Gly Gln His Pro Ser Leu Glu Glu Leu Gln Glu Val Val Val
                420                 425                 430

His Lys Lys Met Arg Pro Thr Ile Lys Asp His Trp Leu Lys His Pro
                435                 440                 445

Gly Leu Ala Gln Leu Cys Val Thr Ile Glu Glu Cys Trp Asp His Asp
                450                 455                 460

Ala Glu Ala Arg Leu Ser Ala Gly Cys Val Glu Glu Arg Val Ser Leu
465                 470                 475                 480

Ile Arg Arg Ser Val Asn Gly Thr Thr Ser Asp Cys Leu Val Ser Leu
                485                 490                 495

Val Thr Ser Val Thr Asn Val Asp Leu Pro Pro Lys Glu Ser Ser Ile
                500                 505                 510
```